United States Patent [19]
Selsted

[11] Patent Number: 6,008,195
[45] Date of Patent: Dec. 28, 1999

[54] ANTIMICROBIAL PEPTIDES AND METHODS OF USE

[75] Inventor: Michael E. Selsted, Irvine, Calif.

[73] Assignee: The Regents of University of California, Oakland, Calif.

[21] Appl. No.: 08/799,149

[22] Filed: Feb. 14, 1997

Related U.S. Application Data

[60] Provisional application No. 60/011,834, Feb. 16, 1996.

[51] Int. Cl.[6] .............................. C07K 7/08; C07K 14/47; A61K 38/10; A61K 38/17
[52] U.S. Cl. ........................... 514/14; 530/327; 530/350; 514/12; 514/15
[58] Field of Search .................................... 530/327, 350; 514/12, 14, 15

[56] References Cited

U.S. PATENT DOCUMENTS 5,459,235  10/1995  Selsted et al. .......................... 530/300

OTHER PUBLICATIONS

Diamond et al., "Airway epithelial cells are the site of expression of a Mammalian antimicrobial peptide gene", *Proc. Natl. Acad. Sci.*, vol. 90, pp. 4596–4600, May, 1993.

Selsted et al., "Defensins in granules of phagocytic and non–phagocytic cells", *Trends in Cell Biology*, vol. 5, Mar. 1995.

Zanetti et al., The cDNA of the Neutrophil Antibiotic Bac5 Predicts a Pro–sequence Homologous to a Cysteine Proteinase Inhibitor That IS Common to Other Neutrophil Antibiotics, *J. Of Biol. Chem.*, Jan. 5, 1993, vol. 268, No. 1, pp. 522–526.

*Primary Examiner*—Rebecca E. Prouty
*Attorney, Agent, or Firm*—Gray Cary Ware & Freidenrich LLP; Lisa A. Haile

[57] ABSTRACT

Novel antimicrobial peptides from bovine and murine neutrophils are provided. The peptides, designated bovine granulocyte peptide A (BGP-A) and murine granulocyte peptide A (MGP-A) were purified to homogeneity from peripheral blood granulocytes. The amino acid and nucleotide sequence of BGP-A and MGP-A are also provided. A synthetic version of BGP-A and MGP-A is also provided. The purified BGP-A peptide is shown to have antimicrobial activity indistinguishable from that of natural BGP-A. Synthetic carboxamidated analogs of BGP-A (BGP-A-amide) and MGP-A (MGP-A-amide) are also provided.

28 Claims, 5 Drawing Sheets

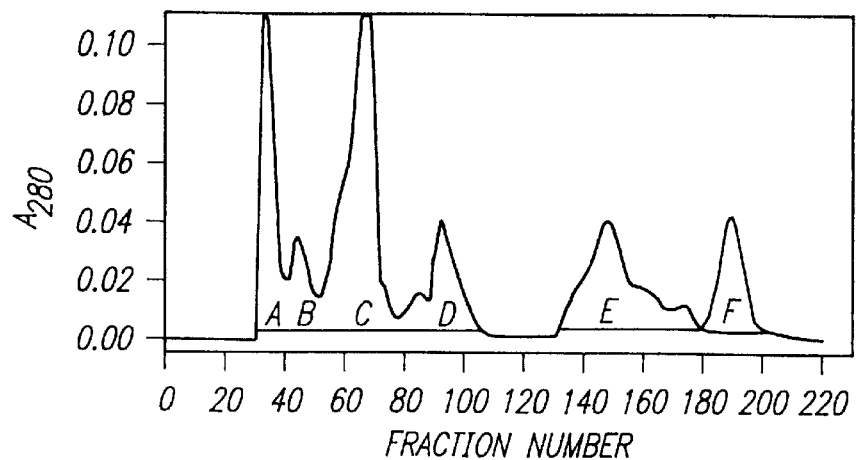
FIG. 1A
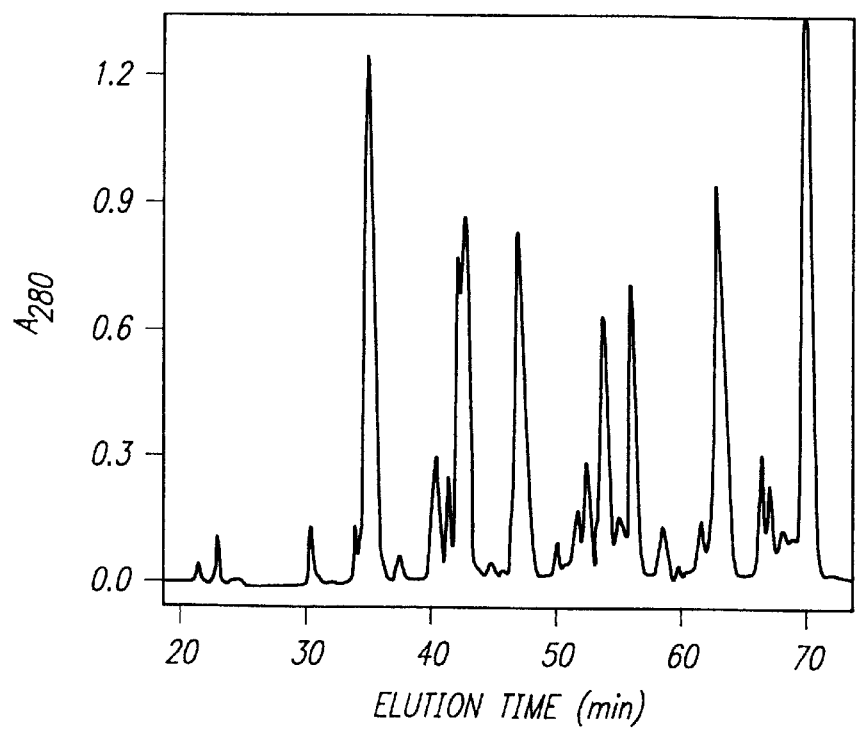
FIG. 1B
FIG. 6
| | | | | | | | | | | | | |
|---|---|---|---|---|---|---|---|---|---|---|---|---|
| BNP-A | Y | K | I | I | Q | Q | W | P | H | Y | R | R | V | 13 |
| MNP-A | Y | Q | V | I | Q | S | W | E | H | Y | R | E | | 12 |

```
AGTCTCCGCGTGTCCTTTCCTGCCTGCCATGTCTCGCCGCTACACACCGC              50
                                M   S   R   R   Y   T   P

TCGCCTGGGTCCTCCTCGCCCTCCTGGGCCTCGGGGCGGCTCAAGACTGC              100
 L   A   W   V   L   L   A   L   L   G   L   G   A   A   Q   D   C

GGCAGCATCGTGTCCCGCGGAAAGTGGGGCGCCCTGGCATCCAAGTGCAG              150
 G   S   I   V   S   R   G   K   W   G   A   L   A   S   K   C   S

CCAGAGGCTAAGACAGCCTGTGCGCTACGTGGTGGTGTCGCACACGGCGG              200
  Q   R   L   R   Q   P   V   R   Y   V   V   V   S   H   T   A

GCAGCGTCTGCAACACTCCGGCCTCGTGCCAGAGGCAGGCCCAAAACGTG              250
 G   S   V   C   N   T   P   A   S   C   Q   R   Q   A   Q   N   V

CAGTACTACCACGTGCGGGAGCGGGGCTGGTGCGACGTGGGCTACAATTT              300
 Q   Y   Y   H   V   R   E   R   G   W   C   D   V   G   Y   N   F

CCTGATCGGAGAAGATGGGCTCGTGTATGAGGGCCGGGGCTGGAACACCT              350
 L   I   G   E   D   G   L   V   Y   E   G   R   G   W   N   T

TAGGTGCTCACTCTGGGCCCACGTGGAACCCCATAGCCATCGGCATCTCC              400
 L   G   A   H   S   G   P   T   W   N   P   I   A   I   G   I   S

TTCATGGGCAACTACATGCATCGGGTGCCCCCGGCCTCTGCTCTCAGGGC              450
 F   M   G   N   Y   M   H   R   V   P   P   A   S   A   L   R   A

GGCCCAGAGTCTGCTGGCTTGTGGCGCAGCTCGGGGATACCTGACTCCTA              500
  A   Q   S   L   L   A   C   G   A   A   R   G   Y   L   T   P

ACTACGAAGTCAAAGGACACCGCGATGTGCAGCAGACGCTCTCTCCAGGG              550
 N   Y   E   V   K   G   H   R   D   V   Q   Q   T   L   S   P   G

GACGAGCTCTATAAAATCATCCAGCAGTGGCCGCACTACCGCCGCGTGTG              600
  D   E   L   Y   K   I   I   Q   Q   W   P   H   Y   R   R   V

AGGGCCTGTCCGTCTTCTCACACCCCACCCATCCCATCAGAAACCCCACC              650

GCCTTCCCCTGCCCCAATAAAGGCGAAGCTTAAACTGT                          688
```

FIG. 4

```
ATACACAGCCCTGCGTCCTGTGCGGCACGTCCAGCATGTTGTTTGCCTGT         50
                                    M   L   F   A   C

GCTCTCCTTGCCCTCCTGGGTCTGGCAACCTCCTGCAGTTTCATCGTGCC        100
 A   L   L   A   L   L   G   L   A   T   S   C   S   F   I   V   P

CCGCAGTGAGTGGAGGGCCCTGCCATCCGAGTGCTCTAGCCGCCTGGGGC        150
 R   S   E   W   R   A   L   P   S   E   C   S   S   R   L   G

ACCCAGTTCGCTACGTGGTGATCTCACACACAGCCGGCAGCTTCTGCAAC        200
 H   P   V   R   Y   V   V   I   S   H   T   A   G   S   F   C   N

AGCCCGGACTCCTGTGAACAGCAGGCCCGCAATGTGCAGCATTACCACAA        250
 S   P   D   S   C   E   Q   Q   A   R   N   V   Q   H   Y   H   K

GAATGAGCTGGGCTGGTGCGATGTAGCCTACAACTTCCTTATTGGAGAGG        300
 N   E   L   G   W   C   D   V   A   Y   N   F   L   I   G   E

ACGGTCATGTCTATGAAGGCCGAGGCTGGAACATCAAGGGTGACCACACA        350
 D   G   H   V   Y   E   G   R   G   W   N   I   K   G   D   H   T

GGGCCCATCTGGAATCCCATGTCTATTGGCATCACCTTCATGGGGAACTT        400
 G   P   I   W   N   P   M   S   I   G   I   T   F   M   G   N   F

CATGGACCGGGTACGCAAAGCGGCCCTCCGTGCTGCCCTAAATCTTCTG        450
 M   D   R   V   R   K   A   A   L   R   A   A   L   N   L   L

GAATCTGGGGTGTCTCGGGGCTTCCTGAGATCCAACTATGAAGTCAAAGG        500
 E   S   G   V   S   R   G   F   L   R   S   N   Y   E   V   K   G

ACACCGGGATGTGCAAAGCACTCTCTCTCCAGGTGACCAACTCTATCAGG        550
 H   R   D   V   Q   S   T   L   S   P   G   D   Q   L   Y   Q

TCATCCAAAGCTGCGAACACTACCGAGAGTGAGAGACCTTGAGACCTAGT        600
 V   I   Q   S   W   E   H   Y   R   E

GAGAATCCCCCCCCCCCAGCCCGAAATCCCTCCTGCCACCTGCTTCTTCC        650

CATTGACCCCCAATAAAGACTCAGCACC                              678
```

FIG. 5

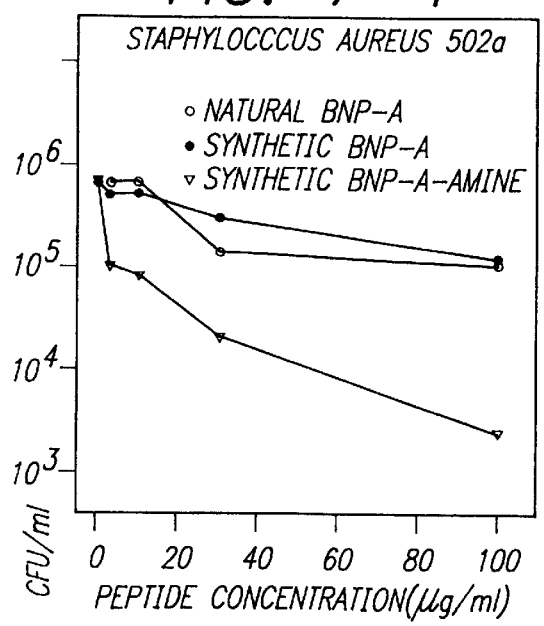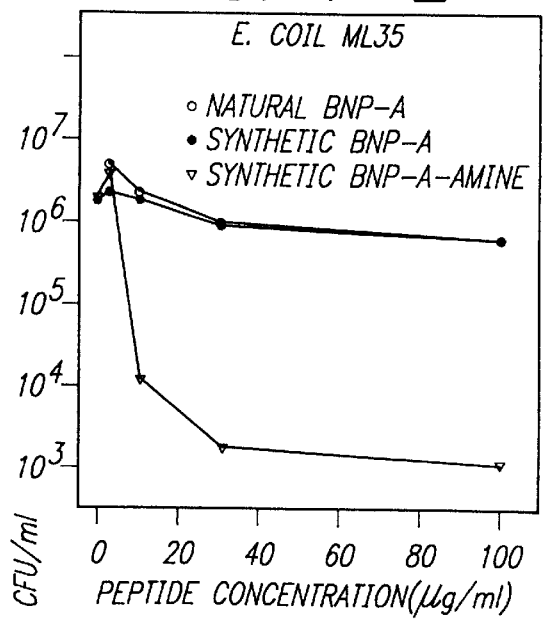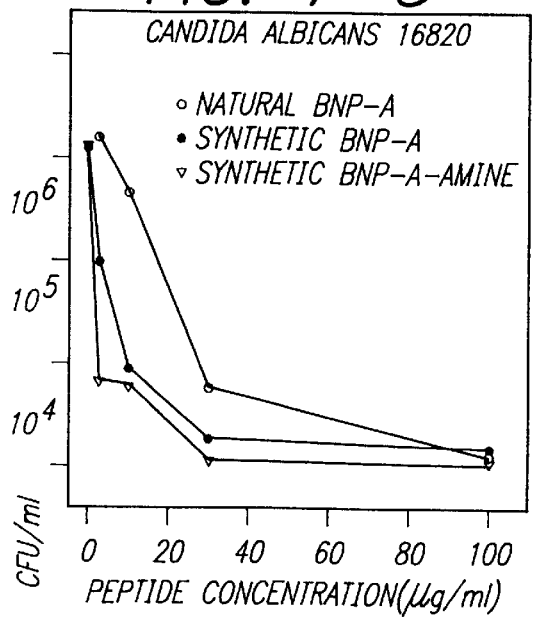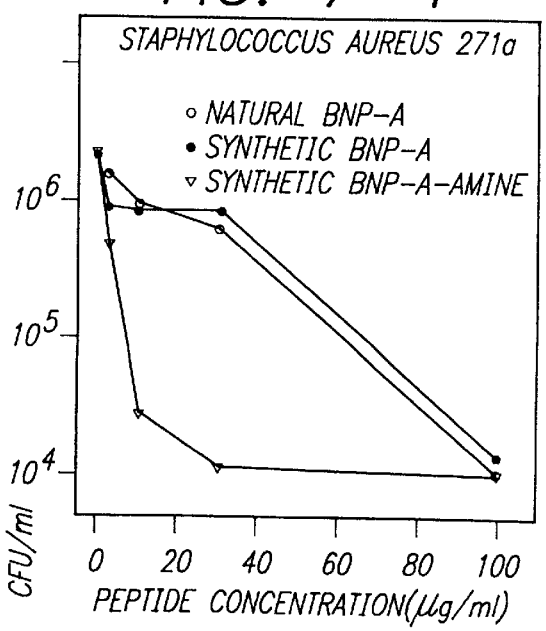

ANTIMICROBIAL PEPTIDES AND METHODS OF USE

This application claims priority from U.S. Provisional Application Ser. No. 60/011,834, filed Feb. 16, 1996.

This invention was made with Government support under Grant No. AI22931 awarded by the National Institutes of Health. The Government has certain rights in this invention.

FIELD OF THE INVENTION

This invention relates generally to antimicrobial peptides, and, more specifically, to peptides designated bovine granulocyte peptide-A (BGP-A), bovine granulocyte peptide-A-amide (BGP-A-amide), murine granulocyte peptide-A (MGP-A) and murine granulocyte peptide-A-amide (MGP-A-amide) and methods of uses thereof.

BACKGROUND OF THE INVENTION

The cytoplasmic granules of polymorphonuclear leukocytes (neutrophils, granulocytes, PMNs) contain antimicrobial peptides that allow these cells to inactivate ingested microbial targets by mechanisms considered "oxygen independent" (Lehrer, R. I. et al., *Blood* 76:2169–2181. 1990). These granule proteins constitute an antimicrobial arsenal that includes defensins (Selsted, M. E., et al, *Trends in Cell Biology* 5:114–119, 1995), β-defensins (Selsted, M. E., et al., *J. Biol. Chem.* 268:6641–6648, 1993), indolicidin (Selsted, M. E., et al.,*J. Biol. Chem.* 267:4292–4295, 1992), and other broad spectrum antibiotic peptides that are released into the phagosome during phagolysosome fusion. To date, members of the defensin family have been isolated from neutrophils of human (Ganz, T., et al., *J. Clin. Invest.* 76:1427–1435, 1985), rabbit (Selsted, M. E., et al., *J. Biol. Chem.* 260:4579–4584, 1985), rat (Eisenhauer, P., et al., *Immun.* 58:3899–3902, 1990), and guinea pig origin (Selsted, M. E., et al., *Infect. Immun.* 55:2281–2286, 1987), and most recently from the Paneth cells of mouse small intestine (Selsted, M. E., et al., *J. Cell Biol.* 118:929–936, 1992). β-defensins have been isolated from the large granules of bovine neutrophils (Selsted, M. E., et al., *J. Biol. Chem.* 268:6641–6648, 1993), bovine tracheal epithelium (Diamond, G. M., et al., *Proc. Natl. Acad. Sci. USA* 88:3952–3956, 1991), and human plasma (Bensch, K. W., et al., *FEBS Lett.* 368:331–335), and indolicidin is a component of the large granules of bovine PMN (Van Abel, R. J., et al., *Int. J. Peptide Protein* 45:401–409, 1995).

The unique features of ruminant granulocytes were first described by Gennaro and Baggiolini and coworkers (Baggiolini, M., et al., *Lab. Invest.* 52:151–158, 1985; Gennaro, R., et al, *J. Cell Biol.* 96:1651–1661, 1983) who demonstrated that neutrophils of cattle, goats, sheep, and ibex are endowed with many unusually large cytoplasmic granules that are distinct from the classical azurophil and specific granules. Subsequent studies established that most of the antibacterial peptides of bovine neutrophils are contained in these unique organelles. Romeo and Gennarro have demonstrated that the large granules of bovine neutrophils contain potent microbicidal peptides that are structurally distinct from defensins (Gennaro, R., et al, *Infect. Immun.* 57:3142–3146, 1989; Romeo, D., et al, *J. Biol. Chem.* 263:9573–9575, 1988). These include three arginine-rich peptides, termed bactenecins, which efficiently kill several gram positive and gram negative bacteria in vitro. Recently, the isolation and characterization of a novel tridecapeptide amide, indolicidin, from bovine neutrophils was reported (Selsted, M. E., et al, *J. Biol. Chem.* 267:42924295, 1992). This cationic peptide was shown to be unusually rich in tryptophan, and to have potent bactericidal activity against *E. coli* and *S. aureus*. More recently the isolation of 13 β-defensins from bovine neutrophils demonstrated that these peptides are covalently dissimilar to defensins, while possessing a similar folded conformation (Selsted, M. E., et al., *J. Biol. Chem.* 268:6641–6648, 1993).

SUMMARY OF THE INVENTION

The present invention provides peptides useful as antimicrobial agents. The invention arose from the discovery of a novel tridecapeptide from bovine peripheral blood granulocytes. The purified peptides and their carboxamide analogs have potent antibacterial, antiviral, antiprotozoal, and antifungal activities. These peptides, designated BGP-A and MGP-A, are effective compounds for use in human and/or veterinary medicine, or as agents in agricultural, food science, or industrial applications for example.

The details of the preferred embodiment of the present invention are set forth in the accompanying drawings and the description below. Once the details of the invention are known, numerous additional innovations and changes will become obvious to one skilled in the art.

BRIEF DESCRIPTION OF THE DRAWINGS

FIGS. 1A & 1B show chromatographs of the purification of BGP-A. FIG. 1*a* shows the gel filtration chromatography of bovine neutrophil granule extract. FIG. 1*b* shows the reversed phase HPLC of the peak E fractions.

FIG. 2*a* shows the analytical RP-HPLC. FIG. 2*b* shows the acid-urea gel of purified BGP-A.

FIG. 4 shows the cDNA nucleotide sequence (SEQ ID NO: 2) and the deduced precursor amino acid peptide sequence (SEQ ID NO: 3) of BGP-A.

FIG. 5 shows the cDNA nucleotide sequence (SEQ ID NO: 4) and the deduced precursor amino acid peptide sequence (SEQ ID NO: 5) of MGP-A.

FIG. 6 shows the mature BGP-A (SEQ ID NO: 6) and MGP-A (SEQ ID NO: 7) amino acid sequences. Hatched area indicates identical amino acids conserved between BGP-A and MGP-A. The consensus peptide amino acid sequence is identified as SEQ ID NO: 1.

FIG. 7, –1, –2, –3, and –4 show the microbicidal activities of natural and synthetic BGP-A and synthetic BGP-A-amide;

FIG. 7–1 shows *Stapylococcus aureus* 502*a*;

FIG. 7–2 shows *E. Coli* ML35;

FIG. 7–3 shows *Candida albicans;* and

FIG. 7–4 shows *Stapylococcus aureus* 271*a*.

DETAILED DESCRIPTION OF THE INVENTION

Figure 2A:
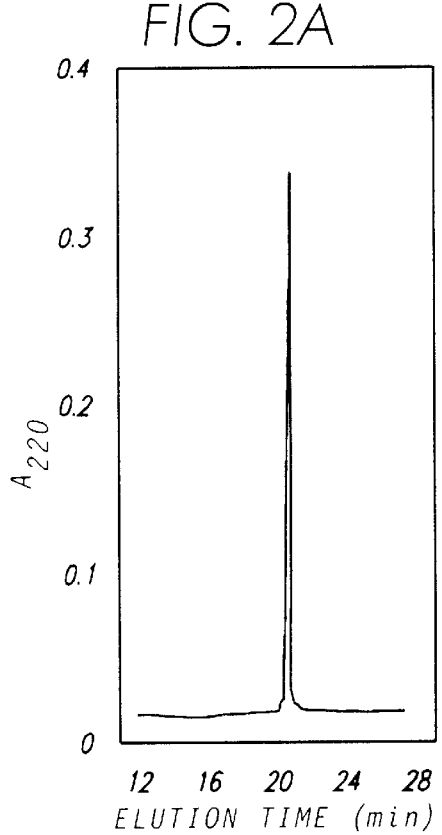
FIGS. 2A and 2B show the analysis of purified BGP-A.

Before the present nucleic and amino acid sequences, compositions, reagents and methods and uses thereof are described, it is to be understood that this invention is not limited to the particular compositions, reagents, sequences and methodologies described herein as such compositions, reagents, sequences and methodologies may vary. It is also to be understood that the terminology used herein is for the purpose of describing particular embodiments only, and that the terminology used herein is not intended to limit the scope of the present invention which will be limited only by the appended claims.

It must be noted that as used herein and in the appended claims, the singular forms "a," "an," and "the," include plural referents unless the context clearly indicates otherwise. Thus, for example, reference to "a reagent" includes one or more of such different reagents, reference to "an antibody" includes one or more of such different antibodies, and reference to "the method" includes reference to equivalent steps and methods known to those of ordinary skill in the art that could be modified or substituted for the methods described herein.

Unless defined otherwise, all technical and scientific terms used herein have the same meaning as commonly understood by one of ordinary skill in the art to which the invention applies. Although any methods, compositions, reagents, sequences similar or equivalent to those described herein can be used in the practice or testing of the invention, the preferred methods and materials are described herein. All publications mentioned herein are incorporated herein, including all figures, graphs, equations, illustrations, and drawings, to describe and disclose specific information for which the reference was cited in connection with.

The publications discussed above are provided solely for their disclosure before the filing date of the present application. Nothing herein is to be construed as an admission that the invention is not entitled to antedate such disclosure by virtue of prior invention. Throughout this description, the preferred embodiment and examples shown should be considered as exemplars, rather than as limitations on the present invention.

During the purification of bovine granulocyte β-defensins, antimicrobial activity associated with a small peptide was detected that was different from any previously characterized. Presented herein is the purification, sequencing, synthesis, cDNA isolation, and antimicrobial properties of BGP-A, a thirteen-residue peptide antibiotic expressed in bovine granulocytes. The cDNA for a mouse homolog of BGP-A, isolated from mouse bone marrow and designated MGP-A, is also presented. The deduced MGP-A precursor was remarkably similar to that of BGP-A. The present invention also teaches the synthesis and antimicrobial properties of BGP-A-amide and MGP-A-amide which are analogs of BGP-A and MGP-A respectively.

The invention provides peptide molecules, designated bovine granulocyte peptide-A (BGP-A) and mouse granulocyte peptide-A (MGP-A) and their synthetic carboxamides, designated BGP-A-amide and MGP-A-amide; which exhibit a broad range of antimicrobial and antiprotozoal activity and consequently, are effective antimicrobial agents. Polynucleotides encoding BGP-A and MGP-A represent a new class of antimicrobial peptide genes. As demonstrated by the high conservation of the precursor structure in a ruminant and a rodent, this gene family appears to be remarkably conserved. In a manner similar to the generating of indolicidin (Selsted, M. E., et al., *Peptides: Chemistry and Biology*, ESCOM J. A. Smith and J. E. Rivier, 1992, pp. 905–907), the peptide is synthesized as a much larger prepropeptide and subsequently packaged in granules as the mature product of proteolytic processing. The methods used for the isolation and purification of BGP-A and MGP-A peptides are similar to those previously used for defensin-like peptides; such methods are taught in U.S. Pat. Nos. 4,453,252, 4,659,692, 4,705,777 and 5,242,902, all of which are incorporated by reference herein in their entirety.

As used herein, the term "antimicrobial activity" refers to the ability of a compound to inhibit or irreversibly prevent the growth of a microorganism. Such inhibition or prevention can be through a microbicidal action or microbistatic inhibition. Therefore, the term "microbicidal inhibition" or "inhibition of microbial growth" as used herein refers to the ability of the antimicrobial peptide to kill, or irrevocably damage the target organism. The term "microbistatic inhibition" as used herein refers to the growth of the target organism without death. Microbicidal or microbistatic inhibition can be applied to an environment either presently exhibiting microbial growth (i.e., therapeutic treatment) or an environment at risk of sustaining or supporting such growth (i.e., prevention or prophylaxis).

As used herein, the term "environment capable of sustaining or supporting microbial growth" refers to a fluid, tissue, space, organ, surface substance or organism where microbial growth can occur or where microbes can exist. Such environments can be, for example, animal tissue; skin or bodily fluids, water and other liquids, food, food products or food extracts, surfaces, crops and certain inanimate objects. It is not necessary that the environment promote the growth of the microbe, only that it permits its subsistence.

The antimicrobial, or antibacterial, activity of BGP-A or MGP-A can be measured against various pathogens by one of ordinary skill in the art. Microorganisms are grown to appropriate concentration, mixed with an appropriate medium, such as an agarosetrypticase soy medium, and contacted with BGP-A or MGP-A. After appropriate incubation, the antimicrobial activity is apparent from clear zones surrounding the antibacterial samples. The clear zones are dependent upon the concentration of the peptide. Further methods of determination of antimicrobial activity are taught in Example 5 and in the section entitled "Materials and Methods" herein and are commonly known by those in the art.

Additionally, the minimum inhibitory concentrations (MIC) of BGP-A or MGP-A to effect antimicrobial activity can be determined for a number of different microorganisms according to standard techniques. Briefly, cells are grown overnight at about 37° C. in appropriate bacterial media and diluted in the same medium to give concentrations of about $10^4$ to $10^5$ CFU/ml. The broth dilutions are set up in a 96 well microtiter plate, for example, mixing combinations of serially diluted microbes and peptides. After additions of serially diluted bacteria, or other microbes with serially diluted peptide concentrations, the plates are incubated overnight at about 37° C. The next day the plates are scored for the presence or absence of microbial growth in the wells, and the MIC is determined from the scoring.

As used herein, the term's BGP-A, BGP-A-amide, MGP-A and MGP-A-amide refer to peptides or peptidomimetics having generally about 8 to 20 amino acids which make up a chain having a net positive charge. In other words, these are cationic peptides. The peptides of the invention preferably have one or more aromatic amino acids. Illustrative peptide sequences are provided in FIGS. 4–6 and as set forth in SEQ ID NOs: 1, 3, 5, 6 and 7.

The full length BGP-A cDNA is 688 nucleotides in length (SEQ ID NO: 2) with a predicted 21 kD precursor protein composed of 190 residues (SEQ ID NO: 3). Within the precursor peptide, 11 of the first 21 residues are hydrophobic and predict a signal peptide. The signal peptide domain is followed by an intervening propeptide region containing 156 residues. The final 13 residues of the precursor correspond to the mature BGP-A peptide sequence, YKIIQQW-PHYRRV (SEQ ID NO: 6).

The full length MGP-A cDNA is 679 nucleotides in length (SEQ ID NO: 4) and predicts a precursor peptide (SEQ ID NO: 4) comprising signal pro-peptide domains similar to those described for BGP-A (FIG. 5). The mature peptide sequence predicted by the murine MGP-A cDNA is identical to BGP-A at 7 of 13 residues (YQVIQSWEHYRE) (FIG. 6; SEQ ID NO: 7). A consensus sequence between the mature BGP and MGP peptides is set forth in FIG. 6 where the hatched area indicates identical amino acids that are conserved between BGP-A and MGP-A and in SEQ ID NO: 1 having an amino acid sequence of YXXIQXWXHYR, where X can be any amino acid. The peptides of the present invention include the SEQ ID NO: 1 consensus sequence. While not wanting to be bound by a particular theory, it is believed that the C-terminus should contain a net positive charge so that the molecule remains active. For example, SEQ ID NO: 1, 6 and 7 all end with an arginine (R) residue, SEQ ID NO: 6 ends with an arginine (R) and valine (V), and SEQ ID NO: 7 ends with a glutamic acid (E) residue. Given that the invention provides both the consensus sequence between mouse and bovine species and the individual DNA sequences encoding the peptides of the present invention, it would not require undue experimentation by the ordinary artisan to isolate homologous BGP/MGP sequences from other species, including human, porcine, ovine, etc., using the teachings supplied herein and methods common in the art (see Maniatis, et al., *Molecular Cloning: A Laboratory Manual,* Cold Spring Harbor Laboratory, Cold Spring Harbor, N.Y., current edition, incorporated herein by reference).

It should be appreciated that various modifications can be made to the BGP-A or MGP-A amino acid sequences without diminishing the antimicrobial activity of the peptides. It is intended that peptides or peptidomimetics of BGP-A or MGP-A exhibiting such modifications, including amino acid additions, deletions or substitutions are within the scope of the invention. As used herein, the term "substantially the same sequence" refers to a peptide sequence either identical to, or having considerable homology with, for example, the sequences BGP-A or MGP-A as shown in FIGS. 4, 5, and 6 and in SEQ ID NOs: 1, 3, 5, 6 and 7. It is understood that limited modifications can be made to the peptide which result in enhanced function. Likewise, it is also understood that limited modifications can be made without destroying the biological function of the peptide and that only part of the entire primary structure may be required to affect activity. For example, minor modifications of these sequences that do not completely destroy the activity also fall within this definition and within the definition of the compound claimed as such. Modifications can include, for example, additions, deletions, or substitutions of amino acid residues, substitutions with compounds that mimic amino acid structure or function as well as the addition of chemical moieties such as amino and acetyl groups. The modifications can be deliberate or can be accidental such as through mutation in hosts that produce BGP-A or MGP-A peptides exhibiting antimicrobial activity. All these modifications are included as long as the peptide retains its antimicrobial activity.

In some cases, it may be desirable to incorporate one or more non-natural amino acids in the synthetic peptides of the present invention. Possible non-natural amino acids will usually have at least an N-terminus and a C-terminus and will have side chains that are either identical to or chemically modified or substituted from a natural amino acid counter part. An example of a non-natural amino acid is an optical isomer of a naturally-occurring L-amino acid. All peptides were synthesized using L amino acids, however, all D forms of the peptides can be synthetically produced. In addition, C-terminal derivatives can be produced, such as C-terminal methyl esters, to increase the antimicrobial activity of a peptide of the invention. Numerous modifications are contemplated according to this invention. Besides the obvious approach of replacement of specific residues in the natural sequence, an alternative embodiment involves synthesis of the peptide from D-amino acids thus reducing potential inactivation by proteases. Such means are well known in the art. (See, for example, Wade et al., *PNAS, USA* 87:4761–4765, 1990.) Examples of chemical modification or substitutions may include hydroxylation or fluorination of C-H bonds within natural amino acids. Such techniques are used in the manufacture of drug analogs of biological compounds and are known to those of ordinary skill in the art. In a preferred embodiment the modification of the peptides of the invention comprises modification by a carboxy terminal amide. Those of skill in the art can make similar substitutions to achieve peptides with greater antimicrobial activity and a broader host range. For example, the invention includes the peptides as set forth in SEQ ID NO: 1, 3, 5, 6 and 7, as well as analogues, derivatives or functional fragments thereof, as long as the antimicrobial activity of the peptide remains. Minor modifications of the primary amino acid sequence of the peptides of the invention may result in peptides which have substantially equivalent antimicrobial activity as compared to the specific peptides as set forth in the SEQ ID NOs: 1, 3, 5, 6 and 7 described herein. Such modifications may be deliberate, as by site-directed mutagenesis, or may be spontaneous. All of the peptides produced by these modifications are included herein as long as the antimicrobial biological activity of the original peptide still exists. BGP-A or MGP-A peptides of the present invention also include functional fragments of the peptide or functional fragments of the nucleic acid sequence encoding the peptide, as long as the activity of BGP-A or MGP-A remains. Smaller peptides containing the biological activity of BGP-A or MGP-A are also included in the invention as are smaller nucleic acid sequences encoding for all or a functional fragment of the peptide. The relative effectiveness of the functional fragments of the peptide or nucleic acid sequences encoding for functional fragments of the peptides of the invention can be readily determined by one of skill in the art by establishing the sensitivity of a microorganism to the peptide fragment. The effectiveness of the peptide functional fragments is assessed by measuring the potential microbicidal or microbistatic activity of the fragment or nucleic acid sequence encoding such a fragment as measured relative to the microbicidal ability of the BGP-A or MGP-A peptides of SEQ ID NO: 6 or 7 respectively. Testing is carried out as described in the section titled "Antimnicrobial Assay" in the Materials and Methods section herein and in Example 5 of the present invention or by other standard antimicrobial tests (e.g., MIC) commonly known to those in the art.

Further, deletion of one or more amino acids can also result in a modification of the structure of the resultant peptide without significantly altering its biological activity. This can lead to the development of a smaller active peptide which would also have utility. For example, amino or carboxy terminal amino acids which may not be required for biological activity of the particular peptide can be removed. Peptides of the invention include any analog, homolog, mutant, isomer or derivative of the peptides disclosed in the present invention, so long as the bioactivity as described herein is remains. The methods and compositions of the present invention may also employ synthetic non-peptide compositions that have biological activity functionally comparable to that of BGP-A, MGP-A, BGP-A-Amide, or MGP-A-Amide. By "functionally comparable," it is meant that the shape, size, flexibility, and electronic configuration of the non-peptide molecule are such that the biological activity of the molecule is similar to the BGP-A, MGP-A, BGP-A-Amide, or MGP-A-Amide peptides. In particular, the non-peptide molecules should display comparable antimicrobial activity. Such non-peptide molecules can be small molecules having a molecular weight in the range of about 100 to 1000 Daltons. The use of such small molecules is advantageous in the preparation of pharmacological compositions.

The identification of such non-peptide analog molecules can be performed using techniques know in the art of drug design. Such techniques include, but are not limited to, self-consistent field (SCF) analysis, configuration interaction (CF) analysis, and normal mode dynamics computer analysis, all of which are well described in the scientific literature. See, e.g., Rein et al., *Computer-Assisted Modeling of Receptor-Ligand Interactions,* Alan Liss, N.Y., (1989). Preparation of the identified compounds will depend on the desired characteristics of the compounds will involve standard chemical synthetic techniques. See, Cary et al., *Advanced Organic Chemistry,* part B, Plenum Press, New York (1983).

The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted peptide also immunoreact with the unsubstituted peptide.

The BGP-A or MGP-A peptides of the present invention can be synthesized by methods well known in the art, such as through the use of automatic peptide synthesizers, by recombinant methods or well-known manual methods of peptide synthesis. In addition, they can be purified from natural sources such as white blood cells and from bone marrow of a vertebrate, preferably of mammalian origin. Such cells or tissues can be obtained by means well known to those skilled in the art.

The term "substantially pure" as used herein refers to BGP-A or MGP-A nucleic acid or protein which is substantially free of other proteins, lipids, carbohydrates or other materials with which it is naturally associated or that the peptide or protein so designated has been separated from its in vivo cellular environment. Because of the separation and purification, the substantially pure peptides and proteins are useful in ways that the non-separated impure peptides or proteins are not. One skilled in the art can purify BGP-A or MGP-A using standard techniques for protein purification. The substantially pure peptide will yield a single major band on an acid-urea gel. The purity of the BGP-A or MGP-A peptide can also be determined by amino-terminal amino acid sequence analysis and analytical RP-HPLC.

The invention also provides polynucleotides encoding the BGP-A or MGP-A protein. These polynucleotides include DNA, cDNA and RNA sequences which encode BGP-A or MGP-A. It is understood that all polynucleotides encoding all or a portion of BGP-A or MGP-A are also included herein, as long as they encode a peptide with BGP-A or MGP-A activity. Such polynucleotides include naturally occurring, synthetic, and intentionally manipulated polynucleotides. For example, BGP-A or MGP-A polynucleotide may be subjected to site-directed mutagenesis. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of BGP-A or MGP-A peptide encoded by the nucleotide sequence is functionally unchanged. The polynucleotide encoding BGP-A or MGP-A includes the nucleotide sequence in FIGS. 4 and 5 (SEQ ID NOs: 2 and 4), as well as complementary nucleic acid sequences. A complementary sequence may include an antisense nucleotide. When the sequence is RNA, the deoxynucleotides A, G, C, and T of SEQ ID Nos: 2 and 4 are replaced by ribonucleotides A, G, C, and U, respectively. Also included in the invention are fragments of the above-described nucleic acid sequences that are at least 15 bases in length, which is sufficient to permit the fragment to selectively hybridize to DNA (SEQ ID NOs: 2 and 4) that encodes the protein of FIGS. 4 and 5 (SEQ ID NOs: 3 and 5), under physiological conditions.

Also, provided by this invention are the nucleic acid sequences encoding the BGP-A or MGP-A peptides, vectors and host cells containing them and methods of expression to provide recombinantly produced peptides. This method comprises growing the host cell containing a nucleic acid encoding a peptide under suitable conditions such that the nucleic acid is transmitted and/or translated and isolating the peptide so produced.

After the peptide of this invention is isolated, nucleic acids encoding the peptides are isolated by methods well known in the art, infra. These isolated nucleic acids can be ligated into vectors and introduced into suitable host cells for expression. Methods of ligation and expression of nucleic acids within cells are well known in the art, (see Maniatis, et al., *Molecular Cloning: A Laboratory Manual,* Cold Spring Harbor Laboratory, Cold Spring Harbor, N.Y., current edition, incorporated herein by reference).

Specifically disclosed herein is a cDNA sequence containing the active portion of the BGP-A or MGP-A coding sequence. One of skill in the art could now use this sequence to isolate other full length clones. The full length BGP-A cDNA is 688 nucleotides in length (SEQ ID NO: 2) and predicts a 21 kD precursor composed of 190 residues (FIG. 4; SEQ ID NO: 3). Within the BGP-A precursor, 11 of the first 21 residues are hydrophobic and predict a signal peptide (Von Heijne, G., *Eur. J. Biochem.* 133:17–21, 1983). The signal peptide domain is followed by an intervening propeptide region containing 156 residues. The final 13 residues of the precursor correspond to the mature BGP-A peptide sequence (SEQ ID NO: 6). The full-length MGP-A cDNA is 679 nucleotides in length (SEQ ID NO: 4) and predicts a precursor comprising signal pro-peptide domains similar to those described for BGP-A (FIG. 5; SEQ ID NO: 5). Based on this similarity, this sequence isolated from murine bone marrow cDNA is designated as murine neutrophil peptide A (MGP-A; FIG. 5; SEQ ID NOs: 5 and 7). The mature peptide sequence predicted by the murine cDNA is identical to BGP-A at 7 of 13 residues (FIG. 6; SEQ ID NO: 7). The hatched area in FIG. 6 indicates identical amino acids conserved between BGP-A and MGP-A. The consensus peptide amino acid sequence is YXXIQXWXHYR (SEQ ID NO: 1), where X can be any amino acid.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features. The sequences of a pair of nucleic acid molecules (or two regions within a single nucleic acid molecule) are said to be "complementary" to each other if base pairing interactions can occur between each nucleotide of one of the members of the pair and each nucleotide of the other member of the pair. A pair of nucleic acid molecules (or two regions within a single nucleic acid molecule) are said to "hybridize" to each other if they form a duplex by base pairing interactions between them. As known in the art, hybridization between nucleic acid pairs does not require complete complementarity between the hybridizing regions, but only that there is a sufficient level of base pairing to maintain the duplex under the hybridization conditions used.

Hybridization reactions are typically carried out under low to moderate stringency conditions, in which specific and some nonspecific interactions can occur. After hybridization, washing can be carried out under moderate or high stringency conditions to eliminate nonspecific binding. As known in the art, optimal washing conditions can be determined empirically, e.g., by gradually increasing the stringency. Condition parameters that can be changed to affect stringency include, e.g., temperature and salt concentration. In general, the lower the salt concentration and the higher the temperature, the higher the stringency. For example, washing can be initiated at a low temperature (e.g., room temperature) using a solution containing an equivalent or lower salt concentration as the hybridization solution. Subsequent washing can be carried out using progressively warmer solutions having the same salt solution. Alternatively, the salt concentration can be lowered and the temperature maintained in the washing step, or the salt concentration can be lowered and the temperature increased. Additional parameters can be altered to affect stringency, including, e.g., the use of a destabilizing agent, such as formamide.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

Preferably the BGP-A or MGP-A polynucleotide of the invention is derived from a mammalian organism, and most preferably from a mouse, cow, or human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequence relating to the peptide of interest is present. In other words, by using stringent hybridization conditions directed to avoid nonspecific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981).

Therefore, given a partial DNA sequence of the BGP-A or MGP-A gene of interest, one of skill in the art would be able to prepare probes for isolation of a full length cDNA clone, without undue experimentation (see for example, Ausubel, et al., *Current Protocols in Molecular Biology*, Units 6.3–6.4, Greene Publ., 1994; Maniatis, et al., *Molecular Cloning*, Cold Spring Harbor Laboratories, current edition).

The compliment of specific DNA sequences encoding BGP-A or MGP-A can also be obtained by: 1) isolation of double-stranded DNA sequences from the genomic DNA; 2) chemical manufacture of a DNA sequence to provide the necessary codons for the peptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of the three above-noted methods for developing specific DNA sequences for use in recombinant procedures, the isolation of genomic DNA isolates is the least common. This is especially true when it is desirable to obtain the microbial expression of mammalian peptides due to the presence of introns.

The synthesis of DNA sequences is frequently the method of choice when the entire sequence of amino acid residues of the desired peptide product is known. When the entire sequence of amino acid residues of the desired peptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the peptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid*, 11:2325, 1983).

Several types of vectors are available and can be used to practice this invention, e.g., plasmid, DNA and RNA viral vectors, baculoviral vectors, and vectors for use in yeast. When the vector is a plasmid, it generally contains a variety of components including promoters, signal sequences, phenotypic selection genes, origins of replication sites, and other necessary components as are known to those of skill in the art.

Promoters most commonly used in prokaryotic vectors include the lac Z promoter system, the alkaline phosphatase pho A promoter, the bacteriophage λPL promoter (a temperature sensitive promotor), the tac promoter (a hybrid trp-lac promoter regulated by the lag repressor), the tryptophan promoter, and the bacteriophage T7 promoter.

One other useful component of vectors used to practice this invention is a signal sequence. This sequence is typically found immediately 5' to the nucleic acid encoding the peptide, and will thus be transcribed at the amino terminus of the fusion protein. However, in certain cases, the signal sequence has been demonstrated to be at positions other than 5' to the gene encoding the protein to be secreted. This sequence targets the protein to which it is attached across the inner membrane of the bacterial cell. The DNA encoding the signal sequence can be obtained as a restriction endonuclease fragment from any nucleic acid encoding a peptide that has a signal sequence. Suitable prokaryotic signal sequences can be obtained from genes encoding, for example Lamb or OmpF (Wong, et al, *Gene* 68:193, 1983), MalE, PhoA, OmpA and other genes. A preferred prokaryotic signal sequence for practicing this invention is the *E. coli* heat-stable enterotoxin II (STII) signal sequence as described by Chang, et al, *Gene* 55:189, 1987.

Another useful component of the vectors used to practice this invention is a phenotypic selection gene. Typical phenotypic selection genes are those encoding proteins that confer antibiotic resistance upon the host cell. By way of illustration, the ampicillin resistance gene (amp) and the tetracycline resistance gene (tet) are readily employed for this purpose.

Construction of suitable vectors comprising the aforementioned components as well as the gene encoding the desired peptide are prepared using standard recombinant DNA procedures. Isolated DNA fragments to be combined to form the vector are cleaved, tailored, and ligated together in a specific order and orientation to generate the desired vector.

The DNA is prepared according to standard procedures (see Maniatis, et al., *Molecular Cloning: A Laboratory Manual*, Cold Spring Harbor Laboratory, Cold Spring Harbor, N.Y., current edition, incorporated herein by reference). If the DNA fragment is to be ligated into a vector, the vector is at first linearized by cutting with the appropriate restriction endonucleases. The linearized vector can then be treated with alkaline phosphatase or calf intestinal phosphatase. The phosphatasing prevents self-ligation of the vector during the ligation step.

After ligation, the vector with the heterologous gene now inserted is transformed into a suitable host cell. Suitable prokaryotic host cells include *E. coli* strain JM101, *E. coli* K12 strain 294 (ATCC number 31,446), *E. coli* strain W3110 (ATCC number 27,325), *E. coli* X1776 (ATCC number 31, 537), *E. coli* XL-1Blue (Stratagene), and *E. coli* B; however, 5 many other strains of *E. coli*, such as HB101, NM522, NM538, NM539 and many other species and genera of prokaryotes can be used as well. Besides the *E. coli* strains listed above, bacilli such as *Bacillus subtillis,* other enterobacteriaceae such as *Salmonella typhimunium* or *Serratia marcesans* and various Pseudomonas species can all be used as hosts.

Transformation of prokaryotic cells is readily accomplished using calcium chloride or other methods well known to those skilled in the art. Electroporation (Neumann, et al., *EMBO J.* 1:841, 1982) also can be used to transform these cells. The transformed cells are selected by growth on an antibiotic, commonly tetracycline (tet) or ampicillin (amp), to which they are rendered resistant due to the presence of tet and/or amp resistance genes on the vector.

After selection of the transformed cells, these cells are grown in culture and the plasmid DNA (or other vector with the foreign gene inserted) is then isolated. Plasmid DNA can be isolated using methods known in the art. This purified plasmid DNA is then analyzed by restriction mapping and/or DNA sequencing.

Following procedures outlined above, mammalian cell lines such as myeloma (P3-653), hybridoma (SP2/0), Chinese Hamster Ovary (CHO), Green monkey kidney (COSI) and murine fibroblasts (LA92) are suitable host cells for peptide expression. These "mammalian" vectors can include a promoter, an enhancer, a polyadenylation signal, signal sequences and genes encoding selectable markers such as geneticin (neomycin resistance), mycophenolic acid (xanthine guanine phosphoribosyl transferase) or histidinol (histidinol dehydrogenase). Suitable promoters for use in mammalian host cells include, but are not limited to, Ig Kappa, Ig Gamma, Cytomegalovirus (CMV) immediate early, Rous Sarcoma Virus (RSV), Simian virus 40 (SV40) early, mouse mammary tumor (MMTV) virus and metallothionein. Suitable enhancers include, but are not limited to, Ig Kappa, Ig Heavy, CMV early and SV40. Suitable polyadenylation sequences include Ig Kappa, Ig Gamma or SV40 large T antigen. Suitable signal sequences include Ig Kappa, Ig Heavy and human growth hormone (HGH).

When the vector is baculovirus, suitable promoters and enhancer sequences include, but are not limited to, AcMGPV polyhedrin, AcMGPV ETL and AcMGPV p10 sequences. One particularly suitable polyadenylation signal is the polyhedrin AcMGPV. Ig Kappa, Ig Heavy and AcMGPV are examples of suitable signal sequences. These vectors are useful in the following insect cell lines, among others: SF9, SF21 and High 5.

Alternatively, the peptides can be expressed in yeast strains such as PS23-6A, W301-18A, LL20, D234-3, INVSC1, INVSC2, YJJ337. Promoter and enhancer sequences such as gal 1 and pEFT-1 are useful. Vra-4 also provides a suitable enhancer sequence. Sequences useful as functional "origins of replication" include ars1 and 2 $\mu$ circular plasmid.

The invention includes antibodies that are immunoreactive with BGP-A or MGP-A peptides or fragments thereof. Antibodies which consist essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., *Nature,* 256:495, 1975). Anti-BGP-A or MGP-A antibodies can be made by methods conventional in the art. For example, polyclonal antiserum can be raised in appropriate animals, such as rabbits, mice, or rats. BGP-A or MGP-A peptides, either synthetically obtained or naturally obtained, can be used to immunize the animal. The immunogen can then be used to immunize animals by means well known to those skilled in the art. Serum samples are collected until the anti-BGP-A or MGP-A titer is appropriate. Various fractions of the antisera, such as IgG, can be isolated by means well known in the art. Alternatively, BGP-A or MGP-A immunogens can be used to obtain monoclonal antibodies, again by means well known in the art. (See, for example, Harlow et al, *Antibodies: A Laboratory Manual,* Cold Springs Harbor Laboratory, 1988.)

Anti-BGP-A or MGP-A antibodies can be used to detect the presence of BGP-A or MGP-A in biological samples, such as histological samples. An appropriate detectable second antibody can be used to identify the primary antibody attached to the BGP-A or MGP-A by visualization. Means of detection include the use of radioactive nucleotides or enzyme substrates such as peroxidase. For example, anti-BGP-A was produced by standard methods and shown to stain bone marrow preparations from cattle (cytological sample). In particular, granulocytes (e.g., eosinophils) were stained heavily for BNP-A.

The term "antibody" as used in this invention includes intact molecules as well as fragments thereof, such as Fab, Fab', F(ab')$_2$, and Fv that can bind the epitopic determinant. These antibody fragments retain some ability selectively to bind with its antigen or receptor and are defined as follows:
(1) Fab, the fragment that contains a monovalent antigen-binding fragment of an antibody molecule can be produced by digestion of whole antibody with the enzyme papain to yield an intact light chain and part of one heavy chain;
(2) Fab', the fragment of an antibody molecule can be obtained by treating whole antibody with pepsin, followed by reduction, to yield an intact light chain and part of the heavy chain; two Fab' fragments are obtained per antibody molecule;
(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;
(4) Fv, defined as a genetically engineered fragment containing the variable region of the light chain and the variable region of the heavy chain expressed as two chains; and
(5) Single chain antibody ("SCA"), defined as a genetically engineered molecule containing the variable region of the light chain, the variable region of the heavy chain, linked by a suitable peptide linker as a genetically fused single chain molecule.

Methods of making these fragments are known in the art. (See for example, Harlow and Lane, *Antibodies: A Laboratory Manual,* Cold Spring Harbor Laboratory, New York (current edition), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

If needed, polyclonal or monoclonal antibodies can be further purified, for example, by binding to and elution from a matrix to which the peptide or a peptide to which the antibodies are raised is bound. Those of skill in the art will know of various techniques common in the immunology arts for purification and/or concentration of polyclonal antibodies, as well as monoclonal antibodies (See, e.g., Coligan, et al., Unit 9, *Current Protocols in Immunology,* Wiley Interscience, current edition, incorporated by reference).

It is also possible to use the anti-idiotype technology to produce monoclonal antibodies that mimic an epitope. For example, an anti-idiotypic monoclonal antibody made to a first monoclonal antibody will have a binding domain in the hypervariable region that is the "image" of the epitope bound by the first monoclonal antibody.

The phrase "purified antibody" means an antibody that is at least 60%, by weight, free from proteins and naturally-occurring organic molecules with which it is naturally associated. Preferably, the preparation is at least 75%, more preferably 90%, and most preferably at least 99%, by weight, an antibody, e.g., an anti-BGP-A specific antibody. A purified antibody may be obtained, for example, by affinity chromatography using recombinantly-produced protein or conserved motif peptides and standard techniques. The invention can employ not only intact monoclonal or polyclonal antibodies, but also an immunologically-active antibody fragment, such as a Fab, Fab' or (Fab')$_2$ fragments, or a genetically engineered Fv fragment (Ladner et al., U.S. Pat. No. 4,946,788).

"Specifically binds" means an antibody that recognizes and binds a specified protein, e.g., an anti-BGP-A, specific antibody or anti-MGP-A specific antibody, which does not substantially recognize and bind other molecules in a sample which naturally includes protein.

It should be understood that the compositions of the present invention have activity against many microorganisms, such as fungi, bacteria (both gram positive and negative), and protozoa and viruses. Different compositions will have differing degrees of activities toward different organisms. The peptides of the present invention may also be combined with other proteins to act as preservatives to protect the proteins against bacterial degradation. Alternatively, the subject peptides or compositions may be used as preservatives and disinfectants in many formulations, such as contact lens solutions, ointments, shampoos, medicaments, foods, and the like. The amount of peptide employed in the compositions may vary depending upon the nature of the other components, how much protection is required and the intended use of the composition.

In a preferred embodiment, the present invention provides administration of a therapeutic amount of an antimicrobial peptide of the invention. One or more of the peptides disclosed herein, may have utility as antifungal agents, either alone, or as lipid fascicle preparations. The latter approach has been used with success with the non-peptide antifungal drug amphotericin. Specific applications would be dependent on the pathogen targeted. For example, *C. albicans,* the common cause of mucocutaneous fungal disease in AIDS patients, which is extremely susceptible to several β-defensins, might be controlled in these individuals more effectively by a BGP-A or MGP-A based therapeutic or in combination with existing first line drugs. Similarly, BGP-A or MGP-A may be used therapeutically in veterinary medicine. One advantage of the therapeutic use of the present invention is that the peptides exhibit low immunogenicity.

BGP-A or MGP-A, either purified from natural sources or synthetic, can be administered to a subject in need of therapy by various means, including oral administration, preferably in a slow-release type formulation that will avoid release within the stomach. Alternatively, they can be administered through a nasal gastric incubation or transabdominal catheter. Individual species of BGP-A or MGP-A can be administered singly or a combination can be administered simultaneously or sequentially and also with other antimicrobial compositions.

The invention further provides a pharmaceutical composition for treating a human bacterial or fungal infection that comprises the purified peptide of the invention in an amount effective to treat a human bacterial or fungal infection and a pharmaceutically acceptable carrier.

The method of inhibiting the growth of bacteria may further include the addition of antibiotics for combination or synergistic therapy. The appropriate antibiotic administered will typically depend on the susceptibility of the bacteria such as whether the bacteria is gram negative or gram positive, and will be easily discernable by one of skill in the art.

Examples of particular classes of antibiotics useful for synergistic therapy with the peptides of the invention include aminoglycosides (e.g., tobramycin), penicillins (e.g., piperacillin), cephalosporins (e.g., ceftazidime), fluoroquinolones (e.g., ciprofloxacin), carbepenems (e.g., imipenem), tetracyclines and macrolides (e.g., erythromycin and clarithromycin). The method of inhibiting the growth of bacteria may further include the addition of antibiotics for combination or synergistic therapy. The appropriate antibiotic administered will typically depend on the susceptibility of the bacteria such as whether the bacteria is gram negative or gram positive, and will be easily discernable by one of skill in the art. Further to the antibiotics listed above, typical antibiotics include aminoglycosides (amikacin, gentamicin, kanamycin, netilmicin, tobramycin, streptomycin, azithromycin, clarithromycin, erythromycin, erythromycin estolate/ethylsuccinate/gluceptate/lactobionate/stearate), beta-lactams such as penicillins (e.g., penicillin G, penicillin V, methicillin, nafcillin, oxacillin, cloxacillin, dicloxacillin, ampicillin, amoxicillin, ticarcillin, carbenicillin, mezlocillin, azlocillin and piperacillin), or cephalosporins (e.g., cephalothin, cefazolin, cefaclor, cefamandole, cefoxitin, cefuroxime, cefonicid, cefmetazole, cefotetan, cefprozil, loracarbef, cefetamet, cefoperazone, cefotaxime, ceftizoxime, ceftriaxone, ceftazidime, cefepime, cefixime, cefpodoxime, and cefsulodin). Other classes of antibiotics include carbapenems (e.g., imipenem), monobactams (e.g., aztreonam), quinolones (e.g., fleroxacin, nalidixic acid, norfloxacin, ciprofloxacin, ofloxacin, enoxacin, lomefloxacin and cinoxacin), tetracyclines (e.g., doxycycline, minocycline, tetracycline), and glycopeptides (e.g., vancomycin, teicoplanin), for example. Other antibiotics include chloramphenicol, clindamycin, trimethoprim, sulfamethoxazole, nitrofurantoin, rifampin and mupirocin.

In certain embodiments of the invention, the treatment of the soluble proteins comprises size exclusion chromatography, ion-exchange chromatography, or reverse phase, high performance, liquid chromatography. It will be appreciated by one skilled in the art, however, that treatment of soluble proteins to purify peptides may be accomplished by many methods known to those skilled in the art, all of which are contemplated by this invention. Further, in one embodiment of the invention, the treatment of granulocytes to recover granules comprises density gradient centrifugation.

The invention also provides a composition that comprises the purified peptide in an amount effective to kill bacteria or fungi and a suitable carrier. Such composition may be used in numerous ways to combat bacteria or fungi, for example, in household or laboratory antimicrobial formulations using carriers well known in the art.

The compositions of the present invention can comprise the BGP-A, BGP-A-Amide, MGP-A, or MGP-A-Amide, either singly or in combination, incorporated in a physiologically-acceptable-carrier suitable for topical application. The compositions may contain from about 10 ug/ml to 2000 ug/ml, preferably 50 ug/ml to 500 ug/ml. The nature of the carrier will vary depending on the intended area of application. For application to the skin, a cream or an ointment base is usually preferred with suitable bases including lanolin, Silvadene™ (Marion; particularly for the treatment of burns) Aquaphor™ (Duke Laboratories, South Norwalk, Conn.), and the like. It will also be possible to incorporate the BGP-A, BGP-A-Amide, MGP-A, or MGP-A-Amide peptides in natural and synthetic bandages and other wound dressings to provide for continuous exposure of a wound to the peptides. Aerosol applicators may also find use with the present invention.

Where the peptides are to be used as antimicrobial agents, they can be formulated in buffered aqueous media containing a variety of salts and buffers. The salts will for the most parts are alkali and alkaline earth halides, phosphates and sulfates, e.g., sodium chloride, potassium chloride or sodium sulfate. Various buffers may be used, such as citrate, phosphate, HEPES, Tris or the like to the extent that such buffers are physiologically acceptable to the host that is being treated.

Various excipients or other additives may be used, where the compounds are formulated as lyophilized powders, for subsequent use in solution. The excipients may include various polyols, inert powders or other extenders.

Depending on the nature of the formulation and the host, the subject compounds may be administered in a variety of ways. The formulations may be applied topically, by injection, e.g., intravenously, intraperitoneal, nasopharyngeal, etc.

In another aspect of the invention, compositions comprising the purified peptide of the invention in a microbicidal effective amount and a suitable carrier or pharmaceutical composition, or pharmaceutically acceptable carrier may additionally comprise a detergent. The addition of a detergent to such peptide compositions is useful to enhance the antibacterial, antiviral, or antifungal characteristics of the novel peptide of the invention. Although any suitable detergent may be used, the presently preferred detergent is a nonionic detergent, such as Tween 20 or 1% NP40.

The invention also provides a pharmaceutical formulation or composition for treating a human microbial, bacterial, viral, or fungal infection that comprises the purified peptide of the invention or a gene delivery and gene expression vector that can deliver an effective amount of peptide in an amount effective to treat a human microbial bacterial, viral, or fungal infection incorporated into a pharmaceutically acceptable liposome or other delivery vehicle.

"Formulation" means a composition capable of gene delivery and gene expression, which can deliver a nucleotide sequence to, or directly into, a target cell whereupon the formulation containing the nucleotide sequence is incorporated on the cytoplasmic side of the outermost membrane of the target cell and capable of achieving gene expression so that detectable levels of gene expression of the delivered nucleotide sequence are expressed in the target cell. More preferably, after delivery into the cytoplasmic side of the cell membrane the composition is subsequently transported, without undergoing endosomal or lytic degradation, into the nucleus of the target cell in a functional state capable of achieving gene expression so that detectable levels of gene expression of the delivered nucleotide sequence are expressed in the target cell. Expression levels of the gene or nucleotide sequence inside the target cell can provide gene expression for a duration of time and in an amount such that the nucleotide product therein can provide a biologically beneficially effective amount of a gene product or in such an amount as to provide a functionally beneficial biological effect. As used herein, the term formulation can refer to, but is not limited by (either explicitly or implicitly) the following examples: (1) liposome or liposome reagents or liposomal compositions either cationic, anionic or neutral in net character and net charge; (2) DNA, nucleic acid or a nucleic acid expression vector ionically complexed with a polycation/s and a ligand/s such that after attachment of the [DNA+Polycation+Ligand] composition to a cell surface receptor on a target cell via the ligand, the [DNA+Polycation+Ligand] composition can be endocytosed into the target cell and the DNA is subsequently decoupled from the ligand and polycation and delivered to the cell nucleus in a functional condition for subsequent expression. Various alterations in the composition can be envisioned by those of ordinary skill in the art such as including peptide sequences that (a) protect the composition from endosomal lysis after incorporation into the target cell by allowing the composition to leave the lysosomal vesicle, or (b) which act as a nuclear targeting agent, chaperoning the nucleic acid through the pores of the nuclear envelope and into the nucleus of the cell. Similar reagents, which have been previously described, are the asialoglycoprotein-polylysine conjugations (Wu et al., *J. Biol. Chem.* 263:14621, 1988; Wu et al., *J. Biol. Chem.* 264:16985, 1989); (3) naked nucleic acid; (4) compacted nucleic acid or a compacted reagent; or (5) plasmid or naked DNA that can be microinjected (Wolff et al., *Science* 247:1465, 1990); (6) nucleic acid in a viral or retroviral vector composition; and (7) colloidal dispersions (Felgner et al., *Proc. Natl. Acad. Sci. USA* 84:7413, 1987; Ono et al., *Neuroscience Lett.* 117:259, 1990; Brigham et al., *Am. J. Med. Sci.* 298:278, 1989; Staubinger and Papahadjopoulos, *Meth. Enz.* 101:512, 1983). One of ordinary skill in the art will recognize that other compositions for the delivery of nucleotide sequences to target cells may be envisioned.

It will be readily understood by those skilled in the art that any suitable pharmaceutically acceptable liposome may be used as a vehicle for the peptide of the present invention. Such liposomal compositions have activity against many microorganisms similar to the activity of other compositions of this invention discussed in more detail above. Additionally, these compositions may be administered in a variety of conventional and well-known ways as is also discussed in greater detail above.

"Therapeutically effective" as used herein, refers to an amount of formulation, composition, or reagent in a pharmaceutical acceptable carrier that is of sufficient quantity to ameliorate the state of the patient or animal so treated. "Ameliorate" refers to a lessening of the detrimental effect of the disease state or disorder in the recipient of the therapy. The subject of the invention is preferably a human, however, it can be envisioned that any animal can be treated in the method of the instant invention. The term "modulate" means enhance, inhibit, alter, or modify the expression or function of antimicrobial activity in combination with a pharmaceutically acceptable carrier.

Pharmaceutically acceptable carrier preparations for administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient is often mixed with excipients that are pharmaceutically acceptable and compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobial, antioxidants, chelating agents, and inert gases and the like.

Another therapeutic approach included within the invention involves direct administration of reagents or compositions by any conventional administration techniques (for example but not restricted to local injection, inhalation, or administered systemically), to the subject with a microbial, bacterial, viral or fungal disorder. The reagent, formulation or composition may also be targeted to specific cells or receptors by any of the methods described herein. The actual dosage of reagent, formulation or composition that modulates a microbial, bacterial, viral or fungal disorder depends on many factors, including the size and health of an organism, however one of one of ordinary skill in the art can use the following teachings describing the methods and techniques for determining clinical dosages (Spilker B., *Guide to Clinical Studies and Developing Protocols,* Raven Press Books, Ltd., New York, 1984, pp. 7–13, 54–60; Spilker B., *Guide to Clinical Trials,* Raven Press, Ltd., New York, 1991, pp. 93–101; Craig C., and R. Stitzel, eds., *Modern Pharmacology,* 2d ed., Little, Brown and Co., Boston, 1986, pp. 127–33; T. Speight, ed., *Avery's Drug Treatment: Principles and Practice of Clinical Pharmacology and Therapeutics,* 3d ed., Williams and Wilkins, Baltimore, 1987, pp. 50–56; R. Tallarida, R. Raffa and P. McGonigle, *Principles in General Pharmacology,* Springer-Verlag, New York, 1988, pp. 18–20) to determine the appropriate dosage to use; but, generally, in the range of about 0.1 mg/kg to 1000 mg/kg, more specifically between about 1.0 mg/kg and 500 mg/kg, and preferably from about 10 mg/kg and 100 mg/kg inclusive final concentration are administered per day to an adult in any pharmaceutically-acceptable carrier.

The peptides of the present invention can also be used to treat an LPS associated disorder. With reference to an LPS associated disorder, the term "therapeutically effective amount" as used herein for treatment of an LPS associated disorder such as endotoxemia or sepsis refers to the amount of BGP-A or MGP-A peptide sufficient to decrease the subject's response to LPS and decrease the symptoms of an LPS associated disorder, such as sepsis. The term "therapeutically effective" therefore includes that the amount of BGP-A or MGP-A peptide sufficient to prevent, and preferably reduce by at least 50%, and more preferably sufficient to reduce by 90%, a clinically significant increase in the plasma level of LPS. The dosage ranges for the administration of BGP-A or MGP-A peptide are those large enough to produce the desired effect. Generally, the dosage will vary with the age, condition, sex, and extent of the infection with bacteria or other agent as described above, in the patient and can be determined by one skilled in the art. The dosage can be adjusted by the individual physician in the event of any contraindications. In any event, the effectiveness of treatment can be determined by monitoring the level of LPS or LPS associated molecules, such as tumor necrosis factor (TNF), in a patient. A decrease in serum LPS and TNF levels correlates positively with amelioration of the LPS associated disorder.

In a further embodiment, the present invention may be used as a food preservative or in treating food products to eliminate potential pathogens. The latter use might be targeted to the fish and poultry industries that have serious problems with enteric pathogens which cause severe human disease. In another embodiment, BGP-A or MGP-A may be used as disinfectants, for use in any product that must remain microbial free. In a further embodiment, BGP-A or MGP-A may be used as antimicrobials for food crops, either as agents to reduce post harvest spoilage, or expressed transgenically to enhance host resistance. Because of the antibiotic, antimicrobial, and antiviral properties of the peptides, they may also be used as preservatives or sterilants of materials susceptible to microbial or viral contamination. The BGP-A or MGP-A peptides of the invention can be utilized as broad spectrum antimicrobial agents directed toward various specific applications. Such applications include use of the peptides as preservatives in processed foods (organisms including Salmonella, Yersinia, Shigella), either alone or in combination with antibacterial food additives such as lysozymes; as a topical agent (Pseudomonas, Streptococcus) and to kill odor producing microbes (Micrococci). The relative effectiveness of the peptides of the invention for the applications described can be readily determined by one of skill in the art by determining the sensitivity of any organism to one of the peptides.

It is also possible to incorporate the peptides on devices or immaterial objects where microbial growth is undesirable as a method of microbicidal inhibition or microbistatic inhibition of microbial growth in an environment capable of sustaining microbial growth by administering to the devices or immaterial objects a microbicidal or microbistatical effective amount of peptide. Such devices or immaterial objects include, but are not limited to, linens, cloth, plastics, implantable devices (e.g., heart pacemakers, surgical stents), surfaces or storage containers. Coating may be achieved by nonspecific absorption or covalent attachment.

EXAMPLES

The following examples are intended to illustrate but not admitted to limit the invention in any manner, shape, or form (either explicitly or implicitly), nor should they be so construed. While they are typical of those that might be used, other procedures, methodologies, or techniques known to those skilled in the art may be used alternatively.

MATERIALS AND METHODS

Bovine neutrophils. Polymorphonuclear leukocytes (PMN) were purified from 1 L batches of fresh citrated bovine blood. Following sedimentation at 40 minutes at 700×g and 37° C., the erythrocyte column was subjected to 7 seconds of hypotonic lysis, after which isotonicity was restored using 3× phosphate buffered saline. The leukocyte-rich suspension was then sedimented at 120×g (4®C., 15 minutes). Residual erythrocytes were lysed by repeating this procedure 1 or 2 times. Aliquots were removed for quantitation by hemocytometry and differential counts. Preparations obtained by this procedure contained an average of $4\times10^9$ cells per L of whole blood of which 97±3% were neutrophils. Preparations were treated with 2 mM diisopropylfluorophosphate (DFP). Neutrophil preparations were then cooled to 4° C. for 20 minutes and disrupted by nitrogen cavitation in a Parr bomb (Borregaard, N., et al., *J. Cell Biol.* 8 97:52–61, 1983). The cavitate was centrifuged at 800×g for 10 minutes at 4° C., and the granule-containing supernatant was collected. Granules were harvested by centrifugation at 27,000×G for 40 minutes and stored at −80° C.

PMN Granule extracts. Preparations of frozen granules from $1-5\times10^{10}$ PMN were extracted with 5 ml of ice cold 10% acetic acid per $1\times10^9$ cell equivalents. After stirring on ice for 18 hours, the suspension was clarified by centrifugation at 27,000×G for 20 minutes at 4° C. and the supernatants were lyophilized and stored at −70° C.

Size exclusion chromatography. Lyophilized granule extract was dissolved in 10% acetic acid at a concentration of ca. $1\times10^9$ cell equivalents per ml, clarified by centrifugation, and loaded onto a 4.8×110 cm column of BioGel P-60 equilibrated in 5% acetic acid. The column was run at 8° C. with an elution rate of 2 cm per hour, and 15 ml fractions were collected with continuous monitoring at 280 nm.

Reversed phase HPLC (RP-HPLC). Low molecular weight components eluting from the size exclusion column were further resolved by RP-HPLC on a Waters 510 binary system on a 1×25 cm Vydac C-18 column. Water and acetonitrile containing 0.1% trifluoracetic acid (TFA) or 0.13% heptafluorobutyric acid (HFBA) were used for gradient elution. Purified peptides were lyophilized, dissolved in 0.01% acetic acid at 100–500 µg/ml, and stored at −70° C.

Polyacrylamide gel electrophoresis. Sodium dodecyl sulfate (SDS; 14) and acid-urea (Selsted, M. E., et al., *Anal. Biochem.* 155:270–274, 1986) gel electrophoresis were used to the estimate molecular mass and/or purity of protein preparations as previously described (Selsted, M. E., et al., *Infect. Immun.* 45:150–154, 1984).

Amino acid analysis. The amino acid composition of each peptide was determined on 6 N HCl hydrolysates (2 h, 15° C.) of native and performic acid-oxidized, or reduced and alkylated samples (Bidlingmeyer, B. A., et al., *J. Chromatogr.* 336:93–104, 1984). Tryptophan content was determined by sequence analysis and by spectroscopic measurement on a Beckman DU 60 spectrophotometer by the method of Edelhoch (Edelhock, H., *Biochem.* 6:1948–1954).

Sequence Analysis. For sequence analysis, purified BGP-A was subjected to automated Edman sequence analysis. Automated sequence analysis was performed on an Applied Biosystems 475A instrument configured with on-line PTH-amino acid analysis. The sequence was confirmed by comparing the primary structure with the amino acid composition, and cDNA cloning.

Peptide synthesis. BGP-A and BGP-A-amide were synthesized at the 0.4 mmol scale on a Millipore 9050 automated synthesizer by standard Fmoc/BOP/HOBt/NMM activation with a 30 minute coupling time. The starting resin for the free acid peptide was Fmoc-L-Valine-PEG-PS (Millipore), and for peptide amide the starting resin was Fmoc-PAL-PEG-PS (Barany, G., et al., *Intercept*, R. Epton, Andover, England, 1992, pp.29–38; Van Abel, R. J., et al., *Int. J. Peptide Protein* Applicant respectfully requests withdrawal of the rejection. 45:401–409, 1995). Side chain protecting groups were Pmc for arginine, trityl for glutamine and histidine, tBoc for lysine and tBu for tyrosine. Fmoc deprotection was with 2% piperidine and 2% DBU for 15 minutes. Tryptophan and isoleucine were double coupled. Following chain assembly the resin was cleaved and deprotected with reagent K (82.5% TFA, 5% phenol, 5% thioanisol, 5% water and 2.5% ethanedithiol) for 4 hours. The peptide solution was made 30% in acetic acid, extracted with dichloromethane, and the aqueous phase was lyophilized. Purification was performed by RP-HPLC on a 22.5×250 mm preparative Vydak C-18 column using 0.1%TFA and a linear acetonitrile gradient developed at 0.33% per minute. The purified peptides were analyzed by amino acid analysis, acid-urea gel electrophoresis and analytical RP-HPLC.

cDNA isolation and characterization. BGP-A: Total RNA was isolated from bovine bone marrow using the acid guanidinium thiocyanate-phenol extraction method of Chomczynski and Sacchi (Chomczynski, P., et al., *Analyt. Biochem.* 162:156–159, 1987). Bone marrow total RNA (1 mg) was then used with avian reverse transcriptase to synthesize first strand cDNA according to the manufacturer's protocol (5'-RACE System; Life Technologies; Gaithersburg, MD). This cDNA was used as a template for 3'-RACE, in which a degenerate gene specific primer was paired with an oligo $(dT)_{15}$-anchor primer to generate the 3'-end of the BGP-A cDNA. PCR amplification was carried out using the following cycling parameters: 95° C., 1 minutes; 55° C., 1 minutes; 72° C., 1 minutes for 35 cycles. 5'-RACE was carried out in a similar fashion with the exception that first strand cDNA was tailed using terminal tranferase and different gene specific and anchor primers were used. PCR-amplified RACE products were subcloned and sequenced as described previously (Yount, N. Y., et al., *J. Immunol.* 155:4476–4484, 1995). Once the 5'- and 3'-ends of the BGP-A cDNA were known, a PCR product corresponding to the full length BGP-A sequence was generated and characterized by sequence analysis.

Murine bone marrow total RNA and first strand cDNA were generated as for BGP-A. Two gene specific primers were then used to PCR amplify a sequence corresponding to a BGP-A homolog. This sequence was subcloned and sequenced as described above.

Antimicrobial assay. *E. coli* ML35, *S. aureus* 502A, *C. albicans,* and *C. neoformans* were used as target organisms in a microbicidal suspension assay as previously described (Selsted, M. E., *Genetic Engineering: Principles and Methods,* J. K. Setlow, Plenum Press, New York, 1993, pp. 131–147).

Example 1
Purification of BGP-A

Previous electrophoretic analyses of the acid-soluble proteins of bovine PMN granules demonstrated that these preparations contain a complex mixture of proteins varying in size from 1,000 to 200,000 D (Selsted, M. E., et al., *J. Biol. Chem.* 267:4292–4295, 1992). Acetic acid extract of a granule-enriched fraction from $1.3 \times 10^{10}$ neutrophils was chromatographed on a Bio-Gel P-60 column as described above in the section titled, "Materials and Methods."

Approximately $2 \times 10^{10}$ cell equivalents of acid solubilized granule protein was fractionated on a BioGel P-60 column and antibacterial activity in pooled eluent fractions was assayed as described in the "Materials and Methods." Fractions corresponding to Peak E were lyophilized and subjected to further purification by RP-HPLC. Each peak (A–F in FIG. 1A) contained bactericidal activity against *S. aureus* and *E. coli.* Peak F was predominantly comprising indolicidin, a novel thirteen residue antibiotic peptide amide (Selsted, M. E., et al., *J. Biol. Chem.* 267:4292–4295), and Peak E contained at least 13 β-defensins.

Peak E fractions were combined and further purified by HPLC. One tenth of the pooled fractions from Peak E (FIG. 1a) was loaded on a 1×25 cm Vydac C-18 column equilibrated in 0.1% TFA/water (solvent A) at a flow rate of 3.0 ml/min. A linear gradient of acetonitrile (20% to 45%) containing 0.1% TFA (solvent B) was applied at the rate of 0.33% per min. Fractions were collected using the peak cutting mode of a Pharmacia Frac-200 fraction collector.

The initial RP-HPLC purification of Peak E fractions yielded a complex chromatogram (FIG. 1B) in which most peaks contained two or more peptides as determined by acid-urea PAGE. However, BGP-A was eluted as an isolated, virtually pure peak (indicated by the asterisk symbol "*" in FIG. 1B) early in the RP-HPLC chromatogram. Final purification (FIG. 2) was obtained by a second round of RP-HPLC.

Example 2
Amino Acid and Sequence Analysis of BGP-A

Figure 2B:
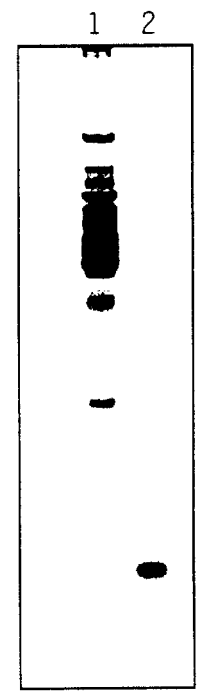

The composition of BGP-A was established by amino acid analysis (FIG. 2). Approximately 5 μg of purified BGP-A was injected onto a 0.4×25 cm Vydac C-18 column run at a flow rate of 1.0 ml/min. Solvents are the same as described above for FIG. 1B. Gradient conditions: 10% B to 50% B in 25 min. B. Acid-urea gel of purified BGP-A. A 2 μg sample of purified BGP-A was loaded onto a 12.5% acid-urea polyacrylamide gel that was electrophoresed for 4 hours at 250 V (lane 2). A 100 μg sample of crude acid extract from bovine neutrophil granules (lane 1) was run in parallel. Staining was with Coomassie Blue containing 15% formalin. Absorbance scans of BGP-A were carried out between 300 and 200 nm, providing an accurate estimate of tyrosine and tryptophan content (Edelhoch, H., *Biochem.* 6:1948–1954, 1967). Automated sequence analysis was carried out on 2 nmol of BGP-A. Repetitive sequencing yields averaged >90 percent, allowing for unambiguous assignment of all thirteen residues. The complete amino acid sequence of BGP-A is:

Tyr-Lys-Ile-Ile-Gln-Gln-Trp-Pro-His-Tyr-Arg-Arg-Val (SEQ ID NO: 5; FIG. 6)

A protein sequence search using the BLAST algorithm (Altschul, S. F., et al., *J. Molec. Biol.* 215:403–410, 1990) revealed no similar amino acid sequences among the GenBank Data base.

Example 3
Synthesis of BGP-A and BGP-A-Amide

Figure 3:
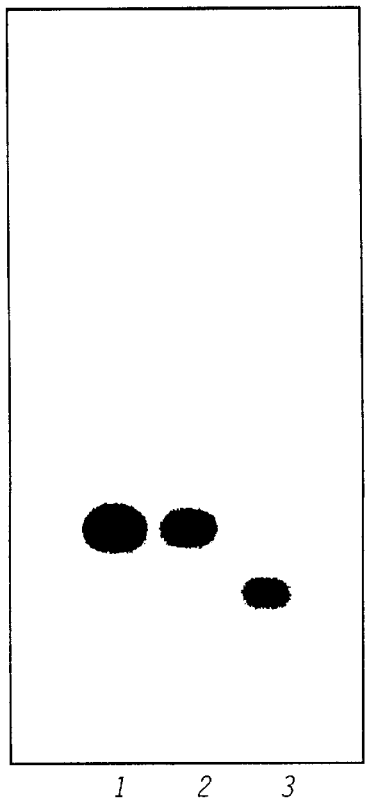
FIG. 3 shows the acid-urea PAGE of purified BGP-A and BGP-A-amide.

The two synthetic BGP-A forms were assembled as $N^\alpha$-Fmoc protected amino acids. (The acid-urea gel patterns of the purified peptides are shown in FIG. 3.) A 12.5% acid-urea gel was loaded with 2–4 μg of natural BGP-A (FIG. 3, lane 1), synthetic BGP-A (FIG. 3, lane 2) or synthetic BGP-A-amide (FIG. 3, lane 3). Staining was as described for FIG. 2. The yields of the HPLC-purified material were 31.4% for the free acid form, and 22.1% for the carboxamidated form.

Example 4
Isolation and Sequencing of BGP-A cDNA Clones

The full length BGP-A cDNA is 688 nucleotides in length (SEQ ID NO: 2) and predicts a 21 kD precursor composed of 190 residues (FIG. 4; SEQ ID NO: 3). Within the BGP-A precursor, 11 of the first 21 residues are hydrophobic and predict a signal peptide (Von Heijne, G., *Eur. J. Biochem.* 133:17–21, 1983). The signal peptide domain is followed by an intervening propeptide region containing 156 residues. The final 13 residues of the precursor correspond to the mature BGP-A peptide sequence (SEQ ID NO: 6).

To determine if the BGP-A precursor was homologous to other nucleotide or protein sequences, a Blast search of the GenBank database was carried out. Some homology between the BGP-A sequence and a partial cDNA sequence isolated from murine adenocarcinoma of unknown tissue origin was identified. Using consensus primers derived from the murine adenocarcinoma and BGP-A sequences, a cDNA encoding a BGP-A like sequence from mouse bone marrow (FIG. 5; SEQ ID NO: 5) was isolated. This full-length cDNA is 679 nucleotides in length (SEQ ID NO: 4) and predicts a precursor comprising signal pro-peptide domains similar to those described for BGP-A (FIG. 5; SEQ ID NO: 5). The mature peptide sequence predicted by the murine cDNA is identical to BGP-A at 7 of 13 residues (FIG. 6; SEQ ID NO: 7). Based on this similarity, this sequence isolated from murine bone marrow cDNA is designated as mouse granulocyte peptide A (MGP-A; FIG. 5; SEQ ID NO: 5 and FIG. 6, SEQ ID NO: 7).

Example 5
Antimicrobial Activity of BGP-A and BGP-A-Amide.

Natural and synthetic BGP-A and synthetic BGP-A-amide were tested for their microbicidal activities against *S. aureus* 502A, *E. coli* ML35, *C. albicans*, and *C. neoformans*. Using a microbicidal suspension assay (Selsted, M. E., *Genetic Engineering: Principles and Methods*, J. K. Setlow, Plenum Press, New York, 1993, pp.131–147), each peptide was tested against the four test organisms with peptide concentrations ranging from 5–100 µg/ml. The bactericidal and fungicidal activities of the three peptide preparations were assessed using a standard microbicidal assay. Organisms were grown to mid-log phase, harvested, and suspended to $2 \times 10^7$ CFU/ml. The incubation mixture contained $1-2 \times 10^6$ CFU/ml, 10 mM sodium phosphate buffer, pH 7.4, and peptide at concentrations up to 100 µg/ml. After 1 h of incubation at 37 C (4 h incubations for *C. neoformans*), serial 10-fold dilutions were plated on Trypticase Soy Agar (bacteria) or *S. abaraud* dextrose agar (fungi), and incubated for 24–48 h at 37 C. Killing was quantitated by colony counting, and plotted as a function of peptide concentration in the incubation.

The data, presented in FIG. 7, reveal the dose-dependent activity of each peptide as measured by the reduction in colony forming units after a 1 or 4 hour incubation interval. These data demonstrate 1) that BGP-A was microbicidal against each organism; 2) that synthetic BGP-A and natural BGP-A were equal in potency, suggesting that the activity of the natural peptide was attributable to the purified compound and not to a contaminant; and 3) that the carboxamidated form of BGP-A is much more potent against most of the targets than is the free-carboxyl form.

The mature peptide was microbicidal in vitro against representative Gram positive and Gram negative bacteria, and yeast forms of two fungi. The antimicrobial activity of the natural peptide was validated by demonstration that synthetic BGP-A had equivalent killing activity.

Example 6
Activity of BGP-A and BGP-A-Amide To Treat an LPS Disorder

The effect of the BGP, MGP, BGP-A and MGP-A peptides of the invention on LPS-induced TNF in macrophages can be determined by those in the art, according to standard methods. For example, macrophage cells are grown by seeding cells into a cell culture flask and incubated at 37° C., 5% $CO_2$ for 1 week. Macrophage cell media [(Dulbecco's Modified Eagle Medium with Hepes buffer 450 ml; 2.4 mM L-glutamine 3 ml (400 mM); Pen/Strep 3 ml ($10^4$ U/ml of Pen, 1 mg/ml strep); and 10% heat inactivated fetal bovine serum (FBS) 50 ml)] is then completely removed from flasks. 10 mls of cell dissociation solution (Sigma) is added to each flask and incubated at 37° C. for 10 minutes. Cells are removed from flasks, diluted in macrophage cell media and centrifuged for approximately six minutes. The cell pellet is resuspended in 5 ml of media/flask used. 100 µl cell suspension is removed and added to 400 µl of trypan blue and cells are counted using a hemocytometer. The cell suspension is diluted to $1 \times 10^6$ cells/ml and 1 ml of suspension is added per well of a 24 well plate. The 24 well plates are incubated at 37° C., 5% $CO_2$ overnight.

After an overnight incubation, the media is aspirated from all the wells. 100 µl of Lipopolysaccharide (LPS) is added at 100 ng/100µl. BGP-A and MGP-A is added at the desired concentrations/100 µl to specified wells. Macrophage cell media is added to a final volume of 1 ml/well. The plates are incubated for six hours at 37° C., 5% $CO_2$. The supernatant is removed from the wells and stored overnight at 4° C. For those wells in which whole bacteria is added directly to the wells, the supernatant is centrifuged in 0.2 µm filter eppendorf tubes for 5 minutes.

The supernatants are then used in cell cytotoxic L929 assay. The samples are transferred to 96 well plates. 50 µl of TNF media is added to all the wells in all the plates except to those wells in the first row. 10µl of murine TNF standard (20 ng/ml) and 90 µl of TNF media is added in duplicate to the plate and diluted 1:2 down the plate to the second to last row. Test samples (75 µl), comprising the supernatants from the macrophage cell assays, are added to separate rows in duplicate and diluted 1:3 to the second to last rows.

TNF-sensitive L929 mouse fibroblast cells are grown by seeding $10^6$ cells into a 162 cm$^2$ cell culture flask and left to grow for 1 week. L929 cells are removed from the flask with 10 mls of trypsin-EDTA/flask and incubated 3–5 minutes. Cell suspension is diluted and centrifuged for 6 minutes. The pellet is resuspended in 5 mls of fresh L929 media/flask and counted (same as macrophage cells). Cell suspension is diluted to $10^6$ cells/ml. 100 µl is used to inoculate each well of the 96 well plates with the supernatants. (L929 Growth Media is the same as macrophage cell media except instead of FBS, 50 mls of 10% heat inactivated horse serum is utilized; TNF Assay Media is the same as macrophage cell media except 4 µg/ml Actinomycin D is added.)

The plates are incubated at 37° C. at 5% $CO_2$ for 2 days. The media is then aspirated and replaced with 100 µl of the dye MTT (0.5 mg/ml) in modified Eagle Medium without phenol red. The plates are then incubated at 37° C. at 5% $CO_2$ for 3 hours. The dye is then removed and replaced with 100 µl of absolute ethanol. The plates are left at room temperature for 10–15 minutes to dissolve the formazan dye crystals.

The plates are read at 570 nm in a ELISA plate reader with 690 nm reference filter. One unit of TNF activity is defined as the amount required to kill 50% of the L929 cells. The TNF level in Units per ml therefore is the reciprocal of the dilution which led to a 50% killing of L929 cells.

It is to be understood that, while the invention has been described with reference to the above detailed description, the foregoing description is intended to illustrate, but not to limit, the scope of the invention. Other aspects, advantages, and modifications of the invention are within the scope of the following claims. All publications, patent applications, patents, and other references mentioned herein are incorporated by reference in their entirety.

What is claimed is:

1. An isolated antimicrobial peptide comprising an amino acid sequence YXXIQXWXHYR (SEQ ID NO: 1), wherein X can be any amino acid.

2. The peptide of claim 1, wherein the amino acid sequence is set forth in SEQ ID NO: 6.

3. The peptide of claim 1, wherein the amino acid sequence is set forth in SEQ ID NO: 7.

4. The peptide of any of claims 1–3, wherein the peptide comprises at least one modified amino acid.

5. The peptide of claim 4, wherein the modified amino acid comprises a carboxy terminal amide.

6. The peptide of claim 1, wherein the peptide exhibits antimicrobial activity against microorganisms selected from the group consisting of gram positive bacteria, gram negative bacteria, fungi and viruses.

7. The peptide of claim 6, wherein the organism is selected from the group consisting of: *S. aureus, E. coli, C. albicans, S. typhimurium,* and *C. neoformans*.

8. An isolated antimicrobial polypeptide having an amino acid sequence as set forth in SEQ ID NO: 3 or antimicrobial fragments thereof.

9. An isolated antimicrobial polypeptide having an amino acid sequence as set forth in SEQ ID NO: 5 or antimicrobial fragments thereof.

10. A method of microbicidal or microbistatic inhibition in an environment capable of sustaining microbial growth comprising administering to the environment a microbicidal or microbistatical effective amount of a peptide having an amino acid sequence of YXXIQXWXHYR (SEQ ID NO: 1), wherein X can be any amino acid.

11. The method of claim 10, wherein the peptide has the amino acid sequence set forth in SEQ ID NO: 6.

12. The method of claim 10, wherein the peptide has the amino acid sequence set forth in SEQ ID NO: 7.

13. The method of claim 10, wherein the peptide has the amino acid sequence set forth in SEQ ID NO: 3, or antimicrobial fragments thereof.

14. The method of claim 10, wherein the peptide has the amino acid sequence set forth in SEQ ID NO: 5, or antimicrobial fragments thereof.

15. The method of claim 10, further comprising at least one additional antimicrobial composition.

16. The method of claim 15, wherein the antimicrobial composition is selected from the group consisting of an antibiotic, an antifungal, and an antiviral agent.

17. The method of claim 16, wherein the antibiotic agent is selected from a class of antibiotic agents selected from the group consisting of amino-glycosides, penicillins, cephalosporins, carbapenems, monobactams, quinolones, tetracyclines, glycopeptides, chloramphenicol, clindamycin, trimethoprim, sulfamethoxazole, nitrofurantoin, rifampin and mupirocin.

18. The method of claim 17, wherein the antibiotic agent is selected from the group consisting of amikacin, gentamicin, kanamycin, netilmicin, tobramycin, streptomycin, azithromycin, clarithromycin, erythromycin, erythromycin estolate/ethylsuccinate/gluceptate/ lactobionate/stearate, penicillin G, penicillin V, methicillin, nafcillin, oxacillin, cloxacillin, dicloxacillin, ampicillin, amoxicillin, ticarcillin, carbenicillin, mezlocillin, azlocillin, piperacillin, cephalothin, cefazolin, cefaclor, cefamandole, cefoxitin, cefuroxime, cefonicid, cefmetazole, cefotetan, cefprozil, loracarbef, cefetamet, cefoperazone, cefotaxime, ceftizoxime, ceftriaxone, ceftazidime, cefepime, cefixime, cefpodoxime, cefsulodin, imipenem, aztreonam, fleroxacin, nalidixic acid, norfloxacin, ciprofloxacin, ofloxacin, enoxacin, lomefloxacin, cinoxacin, doxycycline, minocycline, tetracycline, vancomycin, and teicoplanin.

19. The method of claim 10, wherein the peptide comprises at least one modified amino acid.

20. The method of claim 19, wherein the modified amino acid comprises a carboxy terminal amide.

21. The method of claim 10, wherein the peptide is an effective microbicidal or microbistatic agent against microorganisms selected from the group consisting of gram positive bacteria, gram negative bacteria, fungi and viruses.

22. The peptide of claim 21, wherein the organism is selected from the group consisting of: *S. aureus, E. coli, C. albicans, S. typhimurium,* and *C. neoformans.*

23. The method of claim 10, wherein the environment is an organism.

24. The method of claim 23, wherein the environment is an animal.

25. The method of claim 23, wherein the environment is a human.

26. The method of claim 10, wherein the environment is a food or food product.

27. The method of claim 10, wherein the environment is a water supply.

28. A method of inhibiting protozoan growth comprising contacting a protozoan with an inhibitory effective amount of a peptide selected from the group consisting of SEQ ID NO: 1, 6 and 7.

* * * * *

UNITED STATES PATENT AND TRADEMARK OFFICE
CERTIFICATE OF CORRECTION

PATENT NO. : 6,008,195
DATED : December 28, 1999
INVENTOR(S) : Michael E. Selsted It is certified that error appears in the above-identified patent and that said Letters Patent is hereby corrected as shown below:

Drawings,
Please replace FIG. 6 (also appearing on title page) with the following figure

Please replace FIG. 7-1 and FIG. 7-2, with the following figures

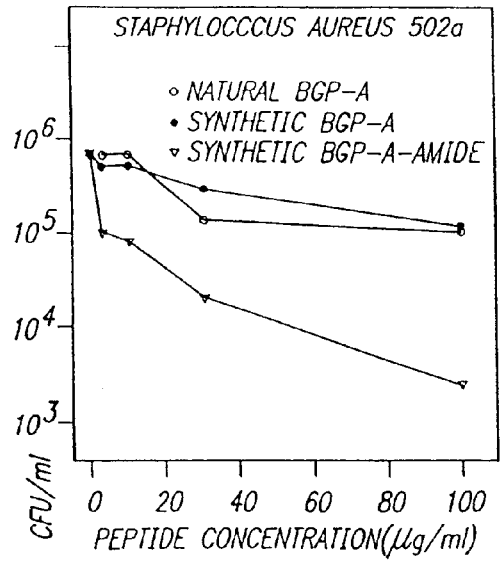
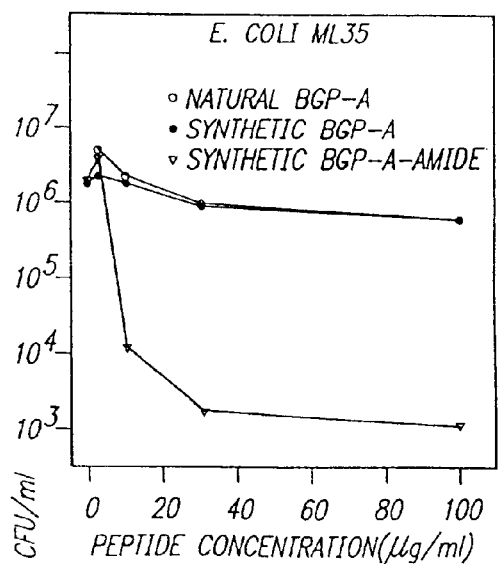

UNITED STATES PATENT AND TRADEMARK OFFICE
CERTIFICATE OF CORRECTION

PATENT NO.      : 6,008,195
DATED           : December 28, 1999
INVENTOR(S)     : Michael E. Selsted It is certified that error appears in the above-identified patent and that said Letters Patent is hereby corrected as shown below:

Drawings (cont'd),
Please replace FIG. 7-3 and FIG. 7-4, with the following figures

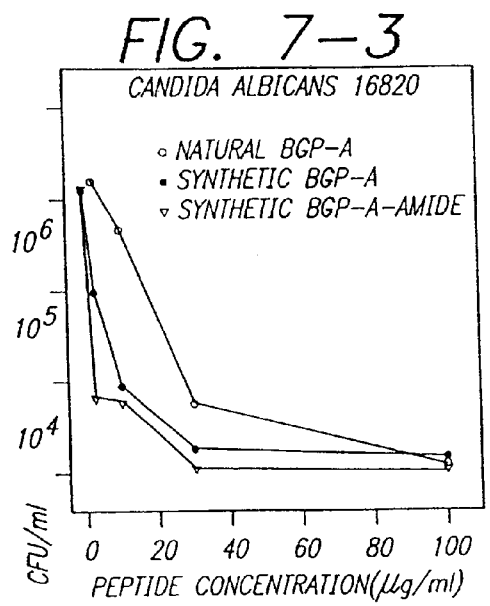
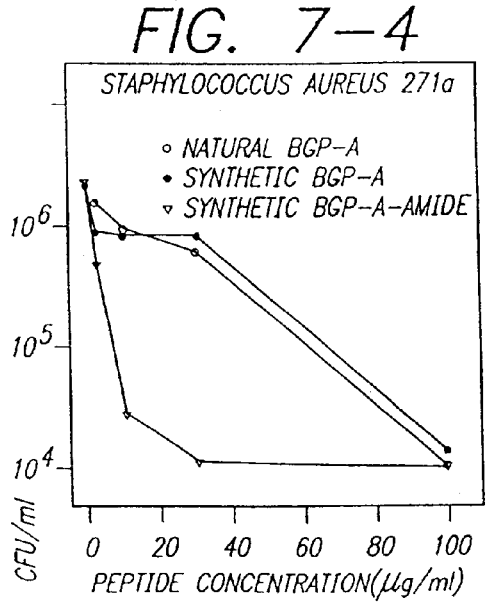

Signed and Sealed this

Sixteenth Day of March, 2004

JON W. DUDAS
*Acting Director of the United States Patent and Trademark Office*

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
       (A) LENGTH: 11 amino acids
       (B) TYPE: amino acid
       (D) TOPOLOGY: linear (ii) MOLECULE TYPE: peptide (ix) FEATURE:
       (D) OTHER INFORMATION: Xaa at amino acid residue 2, 3, 6
          or 8 can be = Ala, Arg, Asn, Asp, Cys, Glu, Gln, Gly, His,
          Ile, Leu, Lys, Met, Phe, Pro, Ser, Thr, Trp, Tyr or Val.

(xi) SEQUENCE DESCRIPTION: SEQ ID NO:1:

```
Tyr Xaa Xaa Ile Gln Xaa Trp Xaa His Tyr Arg
 1               5                  10
```

(2) INFORMATION FOR SEQ ID NO:2:

(i) SEQUENCE CHARACTERISTICS:
       (A) LENGTH: 688 base pairs
       (B) TYPE: nucleic acid
       (C) STRANDEDNESS: single
       (D) TOPOLOGY: linear (ii) MOLECULE TYPE: Genomic DNA (xi) SEQUENCE DESCRIPTION: SEQ ID NO:2:

```
AGTCTCCGCG TGTCCTTTCC TGCCTGCC ATG TCT CGC CGC TAC ACA CCG CTC        52
                                Met Ser Arg Arg Tyr Thr Pro Leu
                                 1               5

GCC TGG GTC CTC CTC GCC CTC CTG GGC CTC GGG GCG GCT CAA GAC TGC      100
Ala Trp Val Leu Leu Ala Leu Leu Gly Leu Gly Ala Ala Gln Asp Cys
     10              15              20

GGC AGC ATC GTG TCC CGC GGA AAG TGG GGC GCC CTG GCA TCC AAG TGC      148
Gly Ser Ile Val Ser Arg Gly Lys Trp Gly Ala Leu Ala Ser Lys Cys
 25              30              35              40

AGC CAG AGG CTA AGA CAG CCT GTG CGC TAC GTG GTG GTG TCG CAC ACG      196
Ser Gln Arg Leu Arg Gln Pro Val Arg Tyr Val Val Val Ser His Thr
             45              50              55

GCG GGC AGC GTC TGC AAC ACT CCG GCC TCG TGC CAG AGG CAG GCC CAA      244
Ala Gly Ser Val Cys Asn Thr Pro Ala Ser Cys Gln Arg Gln Ala Gln
             60              65              70

AAC GTG CAG TAC TAC CAC GTG CGG GAG CGG GGC TGG TGC GAC GTG GGC      292
Asn Val Gln Tyr Tyr His Val Arg Glu Arg Gly Trp Cys Asp Val Gly
             75              80              85

TAC AAT TTC CTG ATC GGA GAA GAT GGG CTC GTG TAT GAG GGC CGG GGC      340
Tyr Asn Phe Leu Ile Gly Glu Asp Gly Leu Val Tyr Glu Gly Arg Gly
     90              95              100

TGG AAC ACC TTA GGT GCT CAC TCT GGG CCC ACG TGG AAC CCC ATA GCC      388
Trp Asn Thr Leu Gly Asp His Ser Gly Pro Thr Trp Asn Pro Ile Ala
105             110             115             120

ATC GGC ATC TCC TTC ATG GGC AAC TAC ATG CAT CGG GTG CCC CCG GCC      436
Ile Gly Ile Ser Phe Met Gly Asn Tyr Met His Arg Val Pro Pro Ala
             125             130             135

TCT GCT CTC AGG GCG GCC CAG AGT CTG CTG GCT TGT GGC GCA GCT CGG      484
Ser Ala Leu Arg Ala Ala Gln Ser Leu Leu Ala Cys Gly Ala Ala Arg
             140             145             150
```

```
GGA TAC CTG ACT CCT AAC TAC GAA GTC AAA GGA CAC CGC GAT GTG CAG        532
Gly Tyr Leu Thr Pro Asn Tyr Glu Val Lys Gly His Arg Asp Val Gln
        155                 160                 165

CAG ACG CTC TCT CCA GGG GAC GAG CTC TAT AAA ATC ATC CAG CAG TGG        580
Gln Thr Leu Ser Pro Gly Asp Glu Leu Tyr Lys Ile Ile Gln Gln Trp
170                 175                 180

CCG CAC TAC CGC CGC GTG TGAGGGCCTG TCCGTCTTCT CACACCCCAC               628
Pro His Tyr Arg Arg Val
185             190

CCATCCCATC AGAAACCCCA CCGCCTTCCC CTGCCCCAAT AAAGGCGAAG CTTAAACTGT      688
```

(2) INFORMATION FOR SEQ ID NO:3:

(i) SEQUENCE CHARACTERISTICS:
        (A) LENGTH: 190 amino acids
        (B) TYPE: amino acid
        (D) TOPOLOGY: linear (ii) MOLECULE TYPE: peptide (ix) FEATURE:
        (A) NAME/KEY: Coding Sequence
        (B) LOCATION: 39..598

(xi) SEQUENCE DESCRIPTION: SEQ ID NO:3:

```
Met Ser Arg Arg Tyr Thr Pro Leu Ala Trp Val Leu Ala Leu Leu
1               5                   10                  15

Gly Leu Gly Ala Ala Gln Asp Cys Gly Ser Ile Val Ser Arg Gly Lys
                20                  25                  30

Trp Gly Ala Leu Ala Ser Lys Cys Ser Gln Arg Leu Arg Gln Pro Val
            35                  40                  45

Arg Tyr Val Val Val Ser His Thr Ala Gly Ser Val Cys Asn Thr Pro
50                  55                  60

Ala Ser Cys Gln Arg Gln Ala Gln Asn Val Gln Tyr Tyr His Val Arg
65                  70                  75                  80

Glu Arg Gly Trp Cys Asp Val Gly Tyr Asn Phe Lys Ile Gly Glu Asp
                85                  90                  95

Gly Lys Val Tyr Glu Gly Arg Gly Trp Asn Thr Lys Gly Asp His Ser
                100                 105                 110

Gly Pro Thr Trp Asn Pro Ile Ala Ile Gly Ile Ser Phe Met Gly Asn
            115                 120                 125

Tyr Met His Arg Val Phe Phe Ala Ser Ala Leu Arg Ala Ala Gln Ser
        130                 135                 140

Leu Leu Ala Cys Gly Ala Ala Arg Gly Tyr Leu Thr Pro Asn Tyr Glu
145                 150                 155                 160

Val Lys Gly His Arg Asp Val Gln Gln Thr Leu Ser Pro Gly Asp Glu
                165                 170                 175

Leu Tyr Lys Ile Ile Gln Gln Trp Pro His Tyr Arg Arg Val
            180                 185                 190
```

(2) INFORMATION FOR SEQ ID NO:4:

(i) SEQUENCE CHARACTERISTICS:
        (A) LENGTH: 677 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:4:

```
ATACACAGCC CTGCGTCCTG TGCGGCACGT CCAGC ATG TTG TTT GCC TGT GCT           53
                                       Met Leu Phe Ala Cys Ala
                                         1               5

CTC CTT GCC CTC CTG GGT CTG GCA ACC TCC TGC AGT TTC ATC GTG CCC         101
Leu Leu Ala Leu Leu Gly Leu Ala Thr Ser Cys Ser Phe Ile Val Pro
            10                  15                  20

CGC AGT GAG TGG AGG GCC CTG CCA TCC GAG TGC TCT AGC CGC CTG GGG         149
Arg Ser Glu Trp Arg Ala Leu Pro Ser Glu Cys Ser Ser Arg Leu Gly
        25                  30                  35

CAC CCA GTT CGC TAC GTG GTG ATC TCA CAC ACA GCC GGC AGC TTC TGC         197
His Pro Val Arg Tyr Val Val Ile Ser His Thr Ala Gly Ser Phe Cys
    40                  45                  50

AAC AGC CCG GAC TCC TGT GAA CAG CAG GCC CGC AAT GTG CAG CAT TAC         245
Asn Ser Pro Asp Ser Cys Glu Gln Gln Ala Arg Asn Val Gln His Tyr
55                  60                  65                  70

CAC AAG AAT GAG CTG GGC TGG TGC GAT GTA GCC TAC AAC TTC CTT ATT         293
His Lys Asn Glu Leu Gly Trp Cys Asp Val Ala Tyr Asn Phe Leu Ile
                75                  80                  85

GGA GAG GAC GGT CAT GTC TAT GAA GGC CGA GGC TGG AAC ATC AAG GGT         341
Gly Glu Asp Gly His Val Tyr Glu Gly Arg Gly Trp Asn Ile Lys Gly
            90                  95                 100

GAC CAC ACA GGG CCC ATC TGG AAT CCC ATG TCT ATT GGC ATC ACC TTC         389
Asp His Thr Gly Pro Ile Trp Asn Pro Met Ser Ile Gly Ile Thr Phe
        105                 110                 115

ATG GGG AAC TTC ATG GAC CGG GTA CGC AAA GCG GCC CTC CGT GCT GCC         437
Met Gly Asn Phe Met Asp Arg Val Arg Lys Ala Ala Leu Arg Ala Ala
    120                 125                 130

CTA AAT CTT CTG GAA TCT GGG GTG TCT CGG GGC TTC CTG AGA TCC AAC         485
Leu Asn Leu Leu Glu Ser Gly Val Ser Arg Gly Phe Leu Arg Ser Asn
135                 140                 145                 150

TAT GAA GTC AAA GGA CAC CGG GAT GTG CAA AGC ACT CTC TCT CCA GGT         533
Tyr Glu Val Lys Gly His Arg Asp Val Gln Ser Thr Leu Ser Pro Gly
                155                 160                 165

GAC CAA CTC TAT CAG GTC ATC CAA AGC TGG GAA CAC TAC CGA GAG              578
Asp Gln Leu Tyr Gln Val Ile Gln Ser Trp Glu His Tyr Arg Glu
            170                 175                 180

TGAGAGACCT TGAGACCTAG TGAGAATCCC CCCCCCCCAG CCCGAAATCC CTCCTGCCAC        638

CTGCTTCTTC CCATTGACCC CCAATAAAGA CTCAGCACC                               677

(2) INFORMATION FOR SEQ ID NO:5:

(i) SEQUENCE CHARACTERISTICS:
         (A) LENGTH: 181 amino acids
         (B) TYPE: amino acid
         (D) TOPOLOGY: linear (ii) MOLECULE TYPE: peptide (ix) FEATURE:
         (A) NAME/KEY: Coding Sequence
         (B) LOCATION: 36..530

(xi) SEQUENCE DESCRIPTION: SEQ ID NO:5:

Met Leu Phe Ala Cys Ala
                               1               5

Leu Leu Ala Leu Leu Gly Leu Ala Thr Ser Cys Ser Phe Ile Val Pro
            10                  15                  20

Arg Ser Glu Trp Arg Ala Leu Pro Ser Glu Cys Ser Ser Arg Leu Gly
        25                  30                  35

His Pro Val Arg Tyr Val Val Ile Ser His Thr Ala Gly Ser Phe Cys
    40                  45                  50
```

```
Asn Ser Pro Asp Ser Cys Glu Gln Gln Ala Arg Asn Val Gln His Tyr
55              60                  65                  70

His Lys Asn Glu Leu Gly Trp Cys Asp Val Ala Tyr Asn Phe Leu Ile
            75                  80                  85

Gly Glu Asp Gly His Val Tyr Glu Gly Arg Gly Tyr Asn Ile Lys Gly
            90                  95              100

Asp His Thr Gly Pro Ile Trp Asn Pro Met Ser Ile Gly Ile Thr Phe
            105                 110             115

Met Gly Asn Phe Met Asp Arg Val Arg Lys Ala Ala Leu Arg Ala Ala
        120             125             130

Leu Asn Leu Leu Glu Ser Gly Val Ser Arg Gly Phe Leu Arg Ser Asn
135             140             145                 150

Tyr Glu Val Lys Gly His Arg Asp Val Gln Ser Thr Leu Ser Pro Gly
                155             160                 165

Asp Gln Leu Tyr Gln Val Ile Gln Ser Trp Glu His Tyr Arg Glu
            170                 175             180
```

(2) INFORMATION FOR SEQ ID NO:6:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:6:

```
Tyr Lys Ile Ile Gln Gln Trp Pro His Tyr Arg Arg Val
1               5                   10
```

(2) INFORMATION FOR SEQ ID NO:7:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:7:

```
Tyr Gln Val Ile Gln Ser Trp Glu His Tyr Arg Glu
1               5                   10
```